(12) United States Patent
Wallace et al.

(10) Patent No.: US 7,691,098 B2
(45) Date of Patent: Apr. 6, 2010

(54) PLATFORM LINK WRIST MECHANISM

(75) Inventors: Daniel T. Wallace, Redwood City, CA (US); S. Christopher Anderson, Northamptom, MA (US); Scott Manzo, Shelton, CT (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 755 days.

(21) Appl. No.: 11/436,988

(22) Filed: May 18, 2006

(65) Prior Publication Data
US 2007/0156119 A1  Jul. 5, 2007

Related U.S. Application Data

(63) Continuation of application No. 10/758,050, filed on Jan. 14, 2004, now Pat. No. 7,066,926, which is a continuation of application No. 10/186,176, filed on Jun. 28, 2002, now Pat. No. 6,699,235.

(60) Provisional application No. 60/301,967, filed on Jun. 29, 2001, provisional application No. 60/327,702, filed on Oct. 5, 2001.

(51) Int. Cl.
| | |
|---|---|
| G05G 11/00 | (2006.01) |
| G05G 9/00 | (2006.01) |
| B25J 9/06 | (2006.01) |
| B25J 11/00 | (2006.01) |
| A61B 17/28 | (2006.01) |
| A61B 19/00 | (2006.01) |
| A61B 17/00 | (2006.01) |

(52) U.S. Cl. ............. 606/1; 74/490.06; 74/490.01; 606/914; 606/206; 606/139; 606/130; 606/142; 606/205

(58) Field of Classification Search ............. 606/1, 606/39, 51, 53, 120, 151, 190, 205, 210, 606/237; 623/24
See application file for complete search history.

(56) References Cited

U.S. PATENT DOCUMENTS

| | | | | |
|---|---|---|---|---|
| 4,806,068 A | * | 2/1989 | Kohli et al. | ............. 414/735 |
| 4,919,112 A | | 4/1990 | Siegmund | |
| 4,919,382 A | * | 4/1990 | Forman | ............. 248/178.1 |
| 5,053,687 A | * | 10/1991 | Merlet | ............. 318/568.2 |
| 5,383,888 A | * | 1/1995 | Zvenyatsky et al. | ......... 606/206 |

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

*Primary Examiner*—Henry M Johnson, III
*Assistant Examiner*—Jeffrey B Lipitz

(57) ABSTRACT

The present invention provides a robotic surgical tool for use in a robotic surgical system to perform a surgical operation. The robotic surgical tool includes a wrist mechanism disposed near the distal end of a shaft which connects with an end effector. The wrist mechanism includes a distal member configured to support the end effector, and a plurality of rods extending generally along an axial direction within the shaft and movable generally along this axial direction to adjust the orientation of the distal member with respect to the shaft. Advancement or retraction of a first rod generally along the axial direction tips the base through a first angle. The addition of a second angle allows the distal member to direct the end effector in essentially a compound angle. The robotic surgical tool may also include provisions for roll movement.

14 Claims, 24 Drawing Sheets

U.S. PATENT DOCUMENTS

| | | | |
|---|---|---|---|
| 5,699,695 A * | 12/1997 | Canfield et al. | 74/490.06 |
| 5,740,699 A | 4/1998 | Ballantyne et al. | |
| 5,792,135 A * | 8/1998 | Madhani et al. | 606/1 |
| 6,331,181 B1 * | 12/2001 | Tierney et al. | 606/130 |
| 6,394,998 B1 * | 5/2002 | Wallace et al. | 606/1 |
| 6,418,811 B1 * | 7/2002 | Rosheim | 74/490.06 |
| 6,425,177 B1 | 7/2002 | Akeel | |
| 6,516,681 B1 * | 2/2003 | Pierrot et al. | 74/490.01 |
| 6,658,962 B1 * | 12/2003 | Rosheim | 74/490.05 |
| 7,273,488 B2 * | 9/2007 | Nakamura et al. | 606/205 |
| 2004/0111113 A1 * | 6/2004 | Nakamura et al. | 606/205 |

* cited by examiner

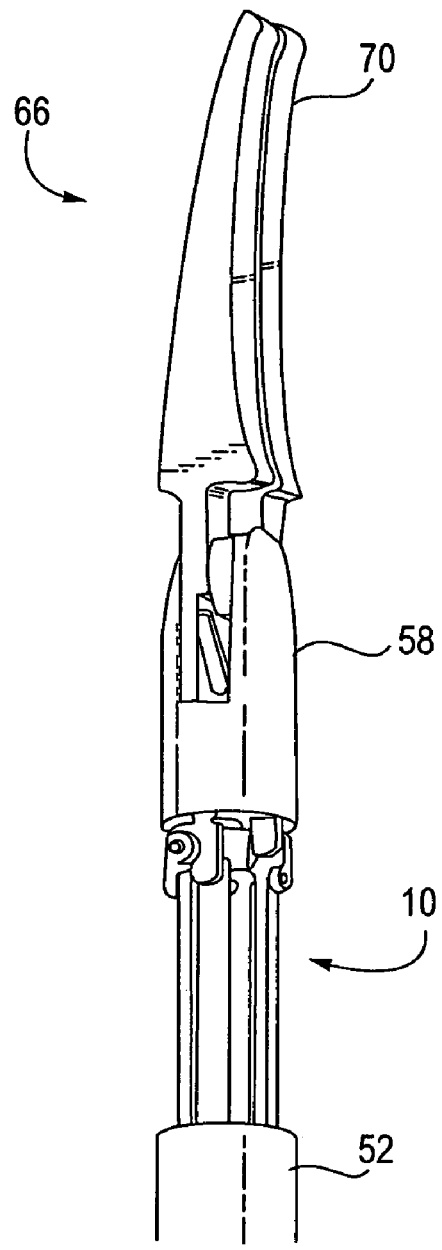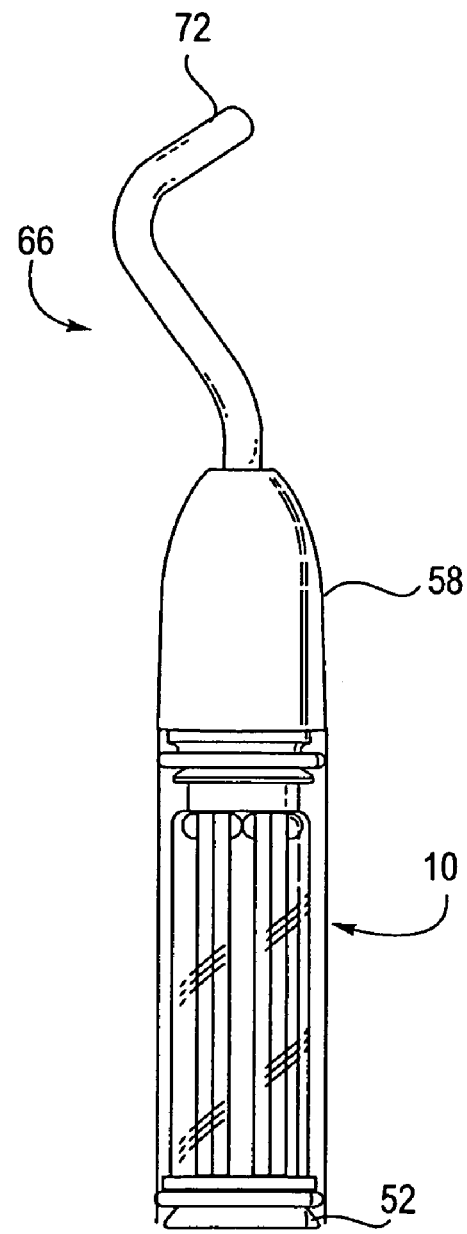
Fig. 2A
Fig. 2B

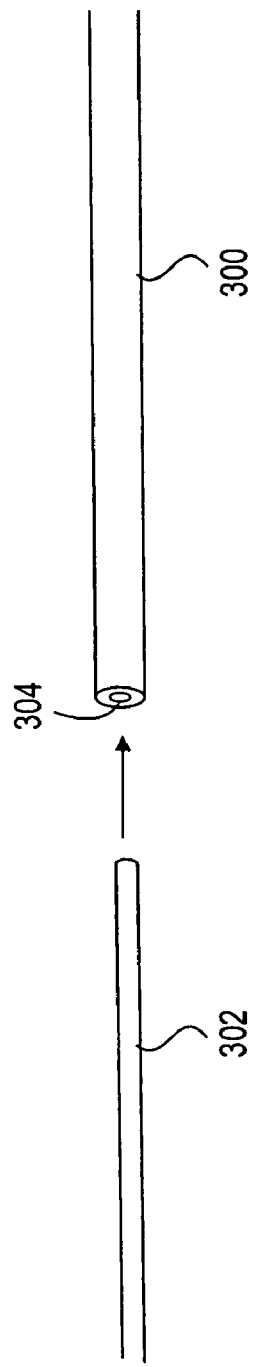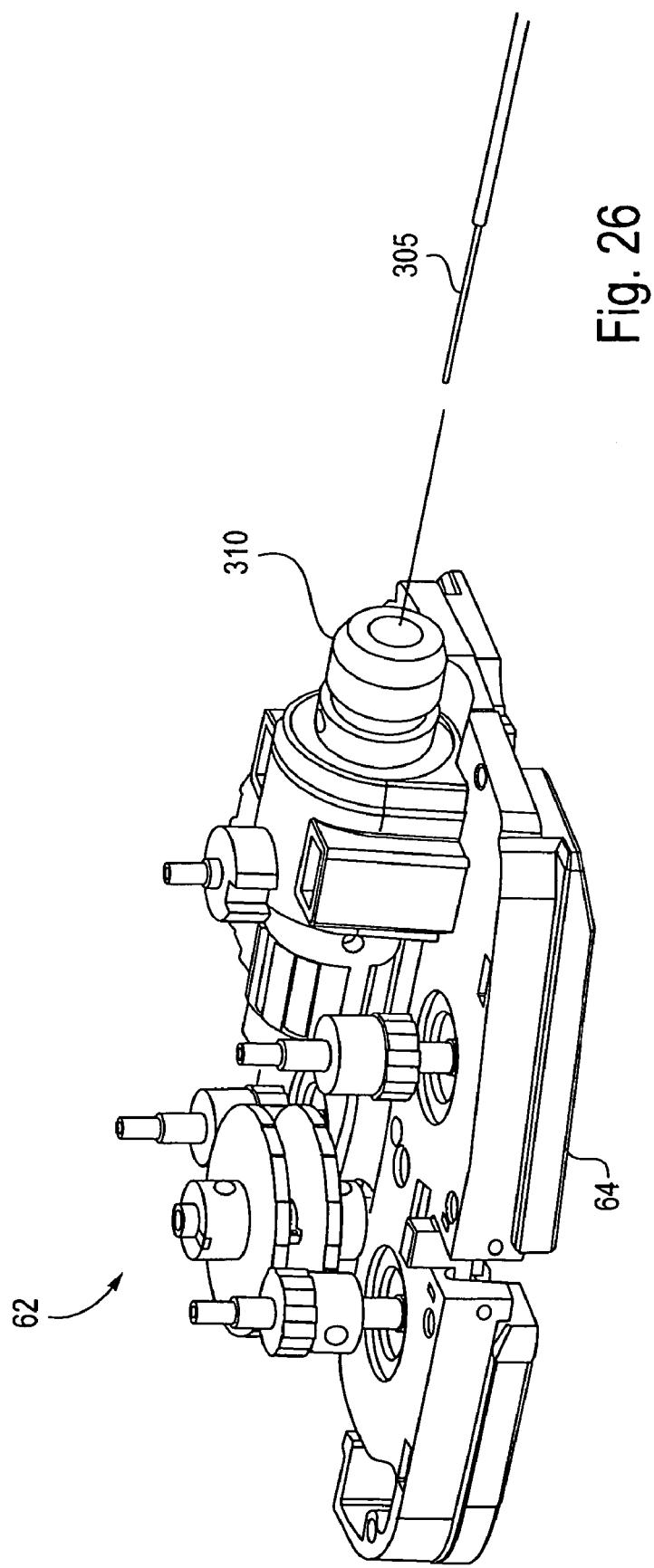

PLATFORM LINK WRIST MECHANISM

CROSS-REFERENCES TO RELATED APPLICATIONS

This application is a continuation of U.S. patent application Ser. No. 10/758,050, filed on Jan. 14, 2004, now U.S. Pat. No. 7,066,926, which is a continuation of U.S. patent application Ser. No. 10/186,176, filed on Jun. 28, 2002, now U.S. Pat. No. 6,699,235, which was based on and claimed the benefit of U.S. Provisional Patent Application No. 60/301,967, filed Jun. 29, 2001, and U.S. Provisional Patent Application No. 60/327,702, filed Oct. 5, 2001, the entire disclosures of which are incorporated herein by reference.

This application is related to the following patents and patent applications, the full disclosures of which are incorporated herein by reference:

PCT International Application No. PCT/US98/19508, entitled "Robotic Apparatus", filed on Sep. 18, 1998, and published as WO99/50721;

U.S. patent application Ser. No. 09/418,726, entitled "Surgical Robotic Tools, Data Architecture, and Use", filed on Oct. 15, 1999;

U.S. Patent Application No. 60/111,711, entitled "Image Shifting for a Telerobotic System", filed on Dec. 8, 1998;

U.S. patent application Ser. No. 09/378,173, entitled "Stereo Imaging System for Use in Telerobotic System", filed on Aug. 20, 1999;

U.S. patent application Ser. No. 09/398,507, entitled "Master Having Redundant Degrees of Freedom", filed on Sep. 17, 1999;

U.S. application Ser. No. 09/399,457, entitled "Cooperative Minimally Invasive Telesurgery System", filed on Sep. 17, 1999;

U.S. patent application Ser. No. 09/373,678, entitled "Camera Referenced Control in a Minimally Invasive Surgical Apparatus", filed on Aug. 13, 1999;

U.S. patent application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

The present invention relates generally to surgical tools and, more particularly, to various wrist mechanisms in surgical tools for performing robotic surgery.

Robotic surgery has developed to improve and expand the use of minimally invasive surgical (MIS) techniques in the treatment of patients. Minimally invasive techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using MIS techniques. Thus, an increased adoption of minimally invasive techniques could save millions of hospital days and millions of dollars annually in hospital residency costs alone. Patient recovery times, patient discomfort, surgical side effects and time away from work may also be reduced with minimally invasive surgery.

The most common form of minimally invasive surgery may be endoscopy. And, probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current MIS technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

Manipulation and control of these end effectors is a critical aspect of robotic surgical systems. For these reasons, it is desirable to provide surgical tools which include mechanisms to provide three degrees of rotational movement of an end effector around three perpendicular axes to mimic the natural action of a surgeon's wrist. Such mechanisms should be appropriately sized for use in a minimally invasive procedure and relatively simple in design to reduce possible points of failure. In addition, such mechanisms should provide adequate degree of rotation to allow the end effector to be manipulated in a wide variety of positions. At least some of these objectives will be met by the inventions described hereinafter.

BRIEF SUMMARY OF THE INVENTION

The present invention provides a robotic surgical tool for use in a robotic surgical system to perform a surgical operation. Robotic surgical systems perform surgical operations with tools which are robotically operated by a surgeon. Such systems generally include master controllers and a robotic arm slave cart. The robotic arm slave cart is positioned adjacent to the patient's body and moves the tools to perform the surgery. The tools have shafts which extend into an internal surgical site within the patient body via minimally invasive access openings. The robotic arm slave cart is connected with master controllers which are grasped by the surgeon and manipulated in space while the surgeon views the procedure on a stereo display. The master controllers are manual input devices which preferably move with six degrees of freedom, and which often further have an actuatable handle for actuating the tools (for example, for closing grasping saws, applying an electrical potential to an electrode, or the like). Robotic surgery systems and methods are further described in co-pending U.S. patent application Ser. No. 08/975,617, filed Nov. 21, 1997, the full disclosure of which is incorporated herein by reference.

As described, robotic surgical tools comprise an elongated shaft having a surgical end effector disposed near the distal end of the shaft. As used herein, the terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment or medical function of a target tissue in the surgical site. The instrument or tool typically includes a shaft carrying the end effector(s) at a distal end, and is preferably servomechanically actuated by a telesurgical system for performing functions such as holding or driving a needle, grasping a blood vessel, and dissecting tissue. In addition, as used herein, "end effector" refers to the actual working part that is manipulable for effecting a predetermined treatment of a target tissue. For instance, some end effectors have a single working member such as a scalpel, a blade, or an electrode. Other end effectors have a pair or plurality of working members such as forceps, graspers, scissors, or clip appliers, for example.

In a first aspect of the present invention, the robotic surgical tool includes a wrist mechanism disposed near the distal end of the shaft which connects with the end effector. The wrist mechanism includes a distal member, configured to support the end effector, and a plurality of rods extending generally along an axial direction within the shaft and movable generally along this axial direction to adjust the orientation of the distal member with respect to the axial direction or shaft. The distal member may have any form suitable for supporting an end effector. In most embodiments, the distal member has the form of a clevis. In any case, the distal member has a base to which the rods are rotatably connected.

Advancement or retraction of a first rod generally along the axial direction tips the base through a first angle so that the distal member faces a first articulated direction. The first angle may be any angle in the range of 0-90 degrees and oriented so that the first articulated direction is any direction that is not parallel to the axial direction. This would allow the distal member to direct an end effector in any direction in relation to the shaft of the surgical tool. In most embodiments, the first angle is greater than approximately 30 degrees. In some embodiments, the first angle is greater than approximately 60 degrees and in other embodiments the first angle is greater than approximately 70 degrees. This first angle may represent the pitch or the yaw of the wrist mechanism.

In some embodiments, advancement or retraction of a second rod generally along the axial direction tips the base through a second angle so that the distal member faces a second articulated direction. The second angle may also be any angle in the range of 0-90 degrees and oriented so that the second articulated direction is any direction that is not parallel to the axial direction. The addition of a second angle would allow the distal member to direct an end effector in essentially a compound angle or in a second articulated direction in relation to the shaft of the surgical tool. In most embodiments, the second angle is greater than approximately 30 degrees. In some embodiments, the second angle is greater than approximately 60 degrees and in other embodiments the second angle is greater than approximately 70 degrees. If the first angle represents the pitch of the wrist mechanism, the second angle may represent the yaw of the wrist mechanism and vice versa.

The plurality of rods may comprise two, three, four or more rods. In preferred embodiments, three or four rods are used to provide both pitch and yaw angulation. When four rods are used, the first and second rods are positioned adjacent to each other and the remaining two rods are located in positions diametrically opposite to the first and second rods. The four rods are generally arranged symmetrically around a central axis of the shaft or the axial direction. When the first rod is advanced, the diametrically opposite rod is simultaneously retracted. Likewise, when the first rod is retracted, the diametrically opposite rod is simultaneously advanced. This is similarly the case with the second rod and its diametrically opposite rod. Thus, the rods actuate in pairs. Such actuation will be further described in a later section.

To maintain desired positioning of the rods, some embodiments include a guide tube having a plurality of guide slots. Each guide slot is shaped for receiving and guiding one of the plurality of rods substantially along the axial direction. In some embodiments, the rods are shaped so as to have a rectangular cross-section. In these instances, the corresponding guide slots also rectangular in shape to receive and maintain proper orientation of the rods.

In a second aspect of the present invention, the robotic surgical tool includes a tool base disposed near the proximal end of the shaft. The tool base includes mechanisms for actuating the wrist mechanism and often mechanisms for actuating the end effector. Mechanisms for actuating the wrist mechanism includes mechanisms for advancing or retracting the first rod. In some embodiments, such mechanisms comprises a first rotational actuation member to which the first rod is attached so that rotation of the first rotational actuation member advances or retracts the first rod. Typically, another rod is attached to the first rotational actuation member in a position diametrically opposite to the first rod so that rotation of the first rotational actuation member simultaneously advances the first rod and retracts the diametrically opposite rod. In some embodiments, the tool base further comprises a second rotational actuation member to which the second rod is attached so that rotation of the second rotational actuation member advances or retracts the second rod substantially along the axial direction. Again, another rod is often attached to the second rotational actuation member in a position diametrically opposite to the second rod so that rotation of the second rotational actuation member simultaneously advances the second rod and retracts the diametrically opposite rod. Thus, by rotating the first and second rotational actuation members, the distal member is tipped through two angles, or a compound angle, so that the distal member faces any desired direction. This allows refined control of the end effector throughout three dimensions.

The robotic surgical tool of the present invention may also include provisions for roll movement. Roll movement is achieved by rotating the shaft around its central axis. Since the shaft is connected to a guide tube through which the plurality of rods pass, rotation of the shaft rotates guide tube which in turn rotates the rods around the central axis which is parallel to the axial direction. To actuate such roll, the above described tool base comprises a roll pulley which rotates the shaft. Since the rods extend through the roll pulley and attach to the rotational actuation members, such rotation is possible by flexing of the rods. Due to the length, thickness and flexibility of the rods, 360 degree rotation is possible. Thus, pitch, yaw and roll movement can be individually actuated by the tool base, particularly by manipulation of the rotational actuation members and roll pulley.

Although actuation of the wrist mechanism is achieved by manipulation of the rods, it is the connection of the rods to the base which allows tipping and manipulation of the distal member to face a desired direction. Such connection is achieved with the use of a plurality of linkages, each linkage connecting one of the plurality of rods with the base. In some embodiments, the linkages comprise orthogonal linkage assemblies. Each orthogonal linkage assembly rotatably connects one of the plurality of rods with the base to allow the base to be rotated in at least two directions with respect to the axial direction. In some embodiments, each orthogonal linkage assembly comprises an orthogonal linkage having a first link portion which is rotatably connectable with the one of the plurality of rods and a second link portion which is rotatably connectable with the base and wherein the first link portion and the second link portion lie in orthogonal planes. In other embodiments, each orthogonal linkage assembly comprises a linkage fastener having a link base portion which is rotatably connectable with one of the plurality of rods and a cylindrical fastening end portion which is rotatably connectable with the base. The different orthogonal linkage assemblies allow the base to be rotated to different degrees of angularity relative to the axial direction.

Such rotation is assisted by flexibility of the rods. Generally, each rod is flexible in at least one direction. For example, when each rod has a rectangular cross-section, having a wide side and a narrow side, the rod may be flexible along the wide side yet rigid along the narrow side. When the rods are arranged so that the wide sides are parallel to the perimeter of the shaft, flexibility along the wide sides allows each rod to bend slightly inward, toward the center of the shaft or the longitudinal axis. This allows greater rotation of the distal member and flexibility in design parameters.

In a third aspect of the present invention, methods of actuating the robotic surgical tool are provided. In some embodiments, methods include providing a robotic surgical tool comprising a wrist mechanism, which includes a distal member coupleable with a surgical end effector and having a base and a plurality of rods rotatably connected to the base and extending along an axial direction, and actuating the wrist by manipulating a first rod of the plurality of rods to tip the base through a first angle so that the distal member faces a first articulated direction. Manipulating typically comprises advancing or retracting the first rod. As previously mentioned, advancing or retracting may comprise rotating a first rotational actuation member to which the first rod is attached. Likewise, actuating the wrist may further comprises manipulating a second rod of the plurality of rods to tip the base through a second angle so that the distal member faces a second articulated direction. Again, advancing or retracting may comprise rotating a second rotational actuation member to which the second rod is attached.

In some embodiments, methods further comprise actuating the wrist by rotating the plurality of rods around a longitudinal axis parallel to the axial direction to rotate the base. In some embodiments, rotating the plurality of rods comprises rotating a roll pulley through which the plurality of rods extend. And, lastly, methods may further comprise coupling the end effector to the base and actuating the end effector.

Other objects and advantages of the present invention will become apparent from the detailed description to follow, together with the accompanying drawings.

BRIEF DESCRIPTION OF THE DRAWINGS

FIGS. 2A-2B illustrate exemplary surgical end effectors.

FIG. 25 illustrates joining of a rod with a wire to create a wire/rod assembly.

FIG. 26 illustrates inserting the wire/rod assembly through a roll pulley within the tool base.

DETAILED DESCRIPTION OF THE INVENTION

Figure 1:
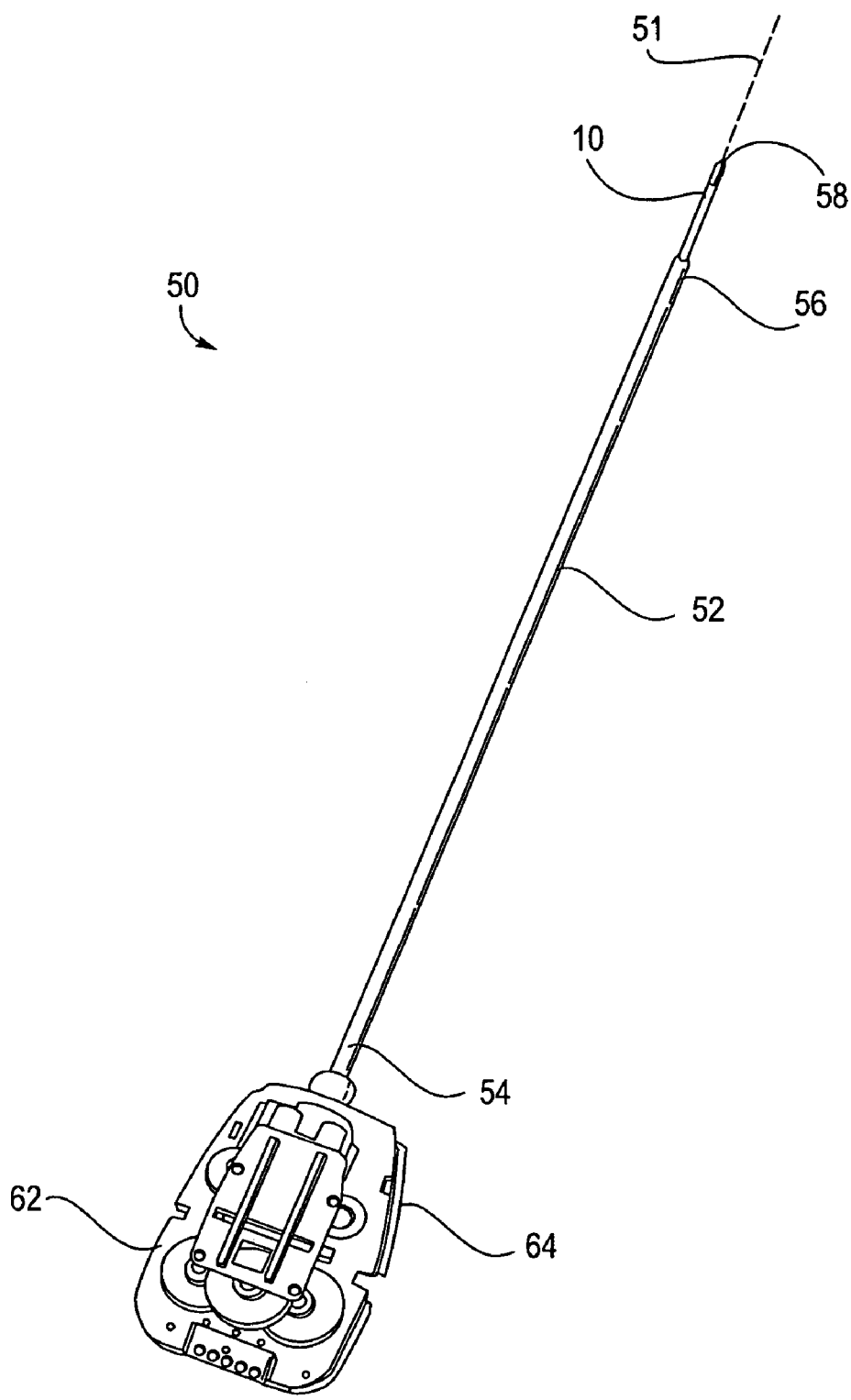
FIG. 1 is a perspective overall view of an embodiment of the surgical tool of the present invention.

FIG. 1 illustrates a surgical tool 50 of the present invention which is used in robotic surgery systems. The surgical tool 50 includes a rigid shaft 52 having a proximal end 54, a distal end 56 and a longitudinal axis therebetween. The proximal end 54 is coupled to a tool base 62. The tool base 62 includes an interface 64 which mechanically and electrically couples the tool 50 to a manipulator on the robotic arm cart. A distal member, in this embodiment a distal clevis 58, is coupled to shaft 52 by a wrist joint or wrist mechanism 10, the wrist mechanism 10 providing the distal clevis 58 with at least 1 degree of freedom and ideally providing at least 3 degrees of freedom. The distal clevis 58 supports a surgical end effector 66, the actual working part that is manipulable for effecting a predetermined treatment of a target tissue. Exemplary surgical end effectors 66 are illustrated in FIGS. 2A-2B. Grasping jaws 70 are illustrated in FIG. 2A, while a cautery isolation effector 72 is illustrated in FIG. 2B. It may be appreciated however that any suitable end effector 66 may be used, such as DeBakey forceps, microforceps, Potts scissors, clip appliers, scalpels or electrocautery probes, to name a few. The end effectors 66 can be permanently attached or be removable and optionally replaceable with a different type of end effector 66 depending on the surgical need.

Figure 3:
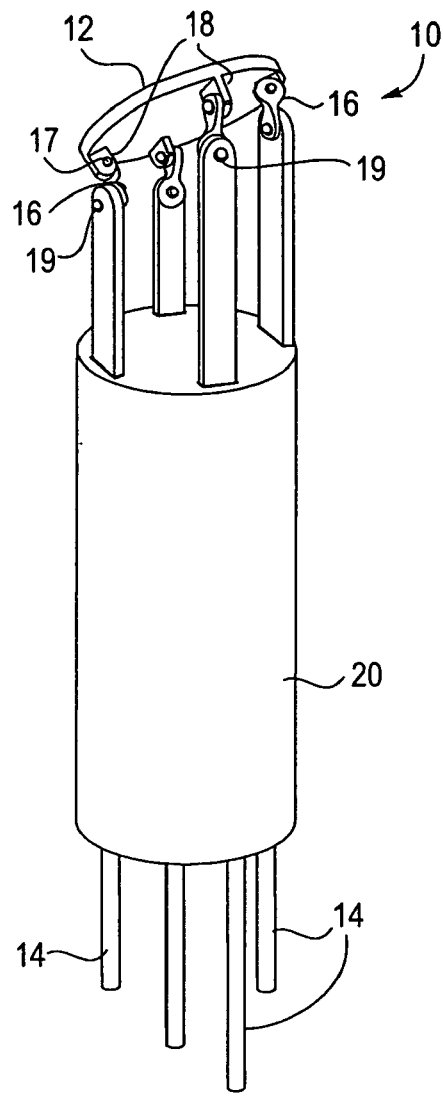
FIG. 3 illustrates an embodiment of a wrist mechanism.
Figure 3C:
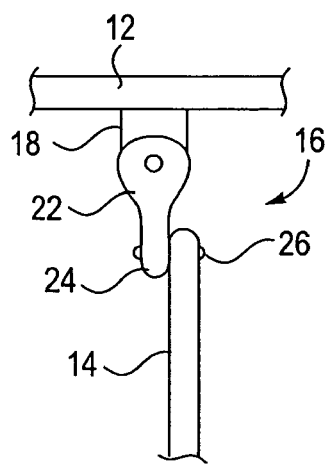
FIGS. 3C-3D illustrate connection of rods to the distal member via orthogonal linkages.
Figure 3D:
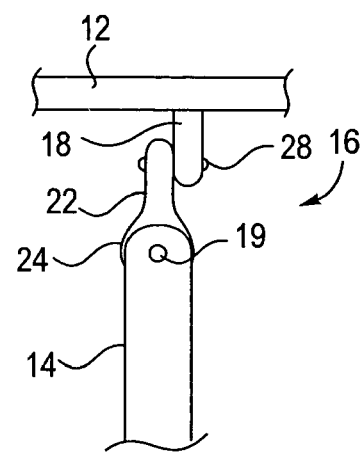
Figure 3A:
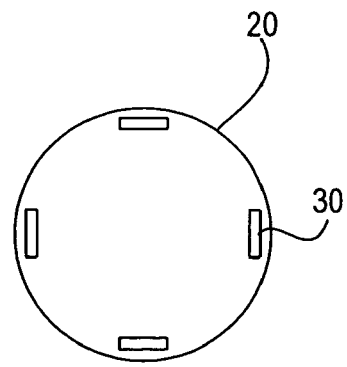
FIGS. 3A-3B illustrate possible arrangements of guide slots within the guide tube.
Figure 3B:
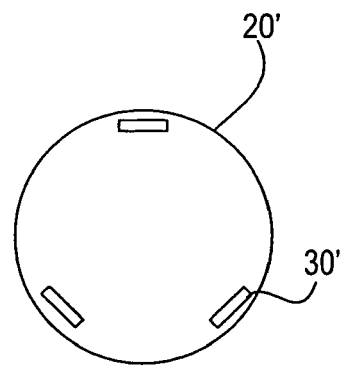

The end effector 66 is manipulated by the wrist mechanism 10 to provide the ability of continuous movement in a wide range of angles (in roll, pitch and yaw) relative to an axial direction or the longitudinal axis 51 of the shaft 52. An embodiment of the wrist mechanism 10 is illustrated in FIGS. 3, 3A-3D. Referring to FIG. 3, the wrist joint or mechanism 10 comprises a distal member 12 connected with a plurality of rods 14 via a plurality of orthogonal linkages 16. Movement of the distal member 12 is directly translated to the surgical end effector 66. In this embodiment, the distal member 12 has the shape of a disk and includes a plurality of feet 18 with apertures 17 which are connected to the orthogonal linkages 16. There are at least three rods, and more desirably four rods 14 as shown in FIG. 3. The rods 14 extend through a guide tube 20 within the shaft 52 (not shown in FIG. 3) which guides and supports the rods 14. FIG. 3A shows the guide tube 20 having four guide slots 30 for receiving the four rods 14. FIG. 3B shows a guide tube 20' having three guide slots 30' for receiving three rods in a different embodiment. The guide slots 30 or 30' are evenly distributed in a generally circular pattern to allow the rods 14 to manipulate and orient the distal member 12 in different directions in a generally continuous manner.

As the rods 14 are slid up and down the guide slots 30 of the guide tube 20, the orthogonal linkages 16 transfer the motion to the distal member 12. The rods 14 are configured to flex in one plane and be stiff in another plane. In the embodiment shown, the rods 14 are flattened to have a rectangular cross-section with a wide face and a narrow width. The rods 14 can flex along the wide face and remain stiff along the narrow width. Referring to FIGS. 3A-3B, the rods 14 can flex toward or away from the center or central axis of the guide tube 20, 20' but remain stiff in terms of side-to-side movement along the perimeter of the guide tube 20, 20'.

The rods 14 include apertures 19 near their distal ends which connect the rods 14 to the distal member 12 via orthogonal linkages 16. Each orthogonal linkage 16 has a first link portion 22 and a second link portion 24 which are oriented in an orthogonal manner, as illustrated in FIGS. 3C-3D. The first link portion 22 includes a first aperture and the second link portion 24 includes a second aperture which is perpendicular in orientation with respect to the first aperture. The second link portion 24 is rotatably coupled to the distal end of the rod 14 by a fastener 26 extending through the apertures of the second link portion 24 and the distal end of the rod 14. The first link portion 22 is rotatably coupled to the feet 18 of the distal member 12 by a fastener 28 extending through the apertures of the first link portion 22 and the feet 18. Because each orthogonal linkage 16 allows relative movement between the rod 14 and the distal member 12 in two orthogonal directions, the distal member 12 can be articulated to move continuously to have orientation in a wide range of angles (in roll, pitch, and yaw) relative to the axial direction of the guide tube 20.

Figure 4:
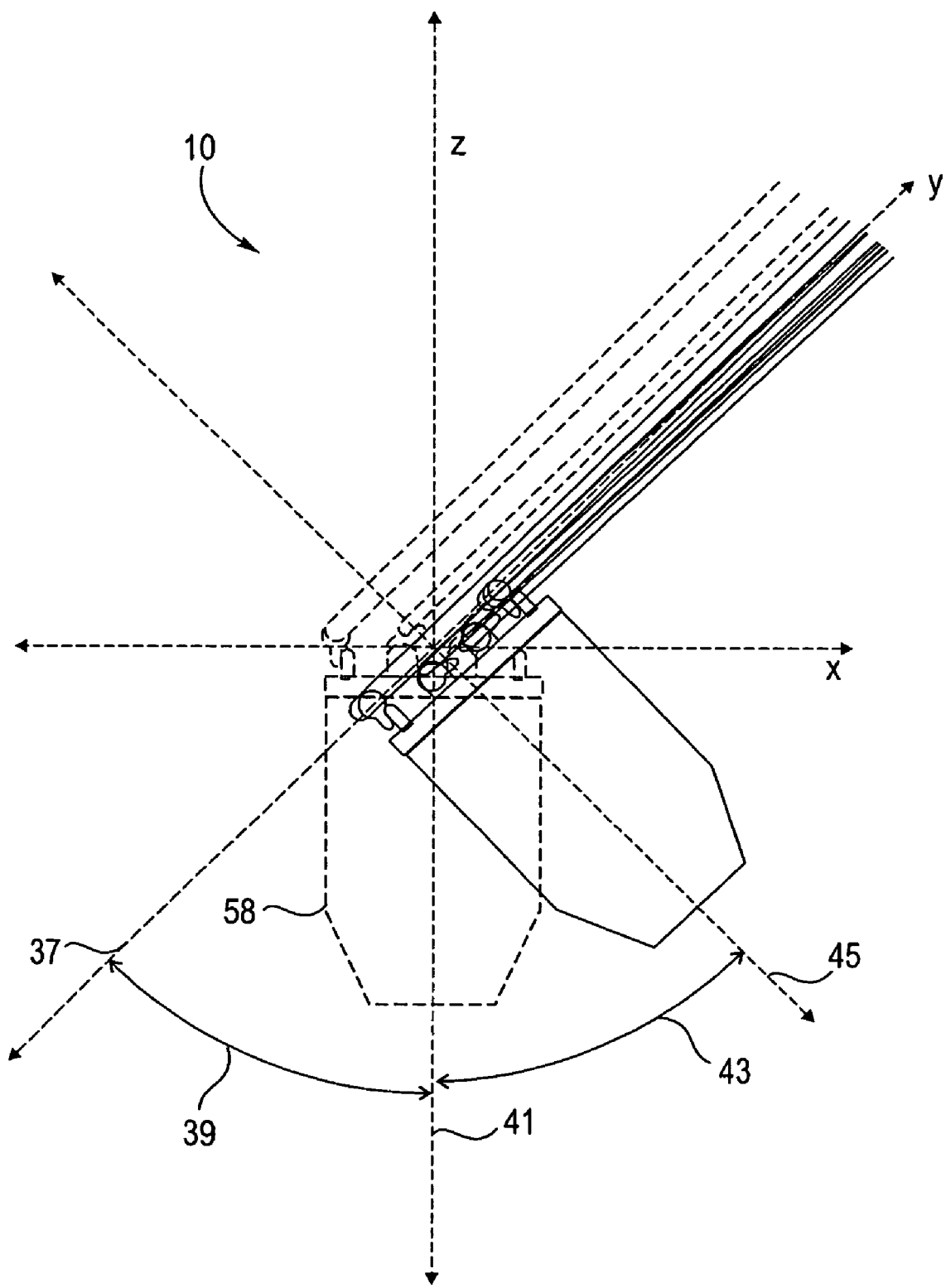
FIG. 4 illustrates movement of the wrist mechanism through a compound angle.

When a first rod is extended generally along the axial direction, the distal member or clevis will be tipped through a first angle. Likewise, when a second rod is extended generally along the axial direction, the distal member or clevis will be tipped through a second angle creating a compound angle. An example of this movement is shown in a simplified illustration in FIG. 4. Here, distal clevis 58 is shown in dashed line having been tipped through a first angle 39 so that the clevis 58 faces a first articulated direction 41. For clarity, the axial direction 37 is aligned with the y-axis and the first articulated direction 41 aligned with the z-axis so that the first angle 39 is formed in a y-z plane. The distal clevis 58 is then tipped through a second angle 43 so that the clevis 58 faces a second articulated direction 45. The second angle 43 is formed in an x-z plane. In this illustration, the first angle 39 represents the pitch and the second angle 43 represents the yaw.

Figure 5:
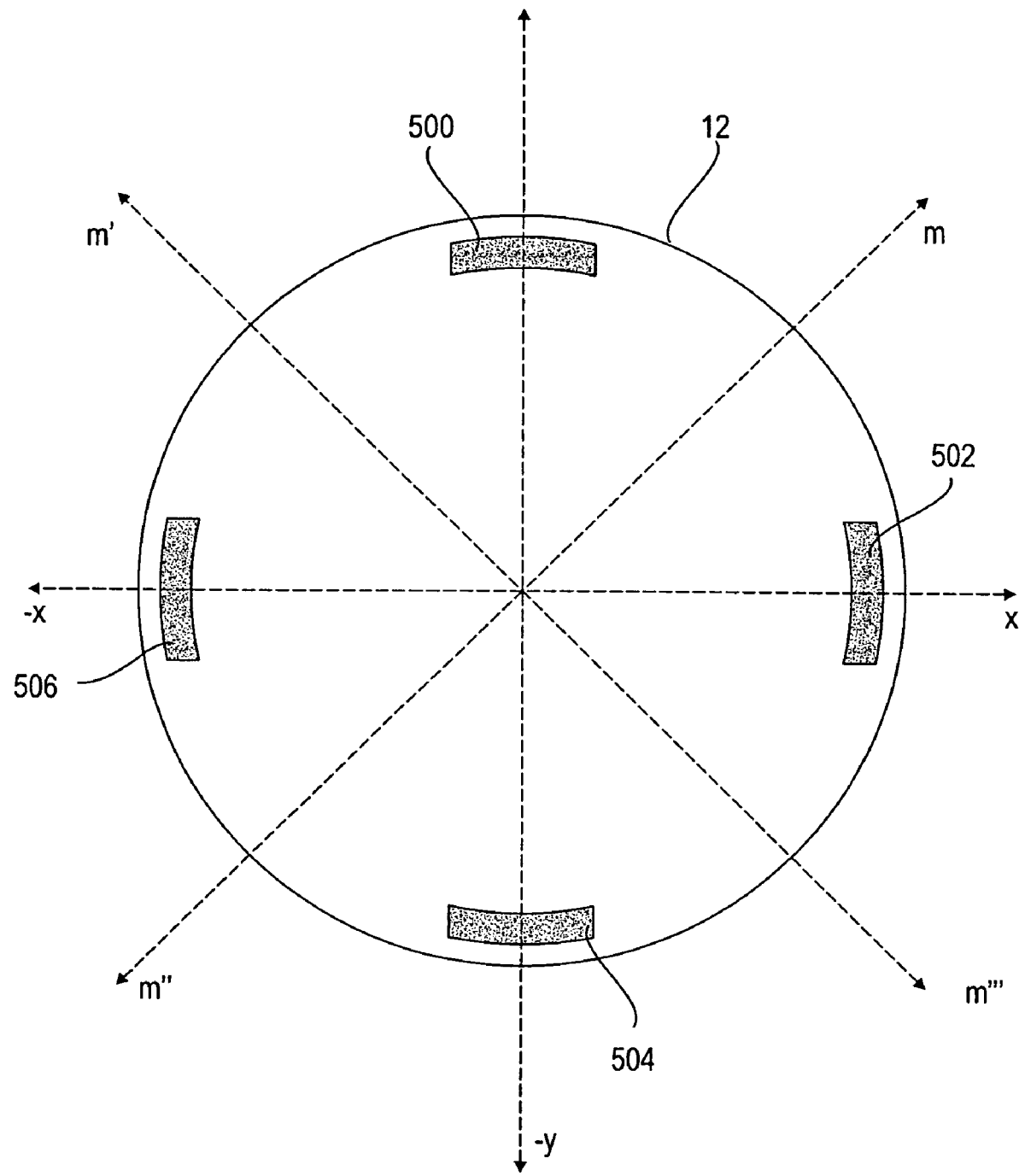
FIG. 5 illustrates tipping in a variety of directions including a combinations of pitch and yaw.

Generally, the range of angles through which the distal member 12 can be articulated varies depending on the combination of pitch and yaw movement. For example, FIG. 5 illustrates a top view of the distal member 12 showing a first rod connection point 500, a second rod connection point 502, a third rod connection point 504 and a fourth rod connection point 506. In this example, a movement of pure pitch would involve rotating the distal member 12 around the y-axis or tipping the distal member toward the x direction or −x direction. This is achieved by advancement of a second rod and corresponding second rod connection point 502 and retraction of a fourth rod and corresponding fourth rod connection point 506, or vice versa. Likewise, in this example, a movement of pure yaw would involve rotating the distal member 12 around the x-axis or tipping the distal member toward the y direction or −y direction. This is achieved by advancement of a first rod and corresponding first rod connection point 500 and retraction of a third rod and corresponding third rod connection point 504, or vice versa. In pure pitch or pure yaw, the distal member 12 can be tipped through angles up to approximately 90 degrees.

However, when the distal member 12 is oriented to face a direction between pure pitch and pure yaw, additional challenges arise in achieving full rotation. In particular, the most challenging position occurs when tipping the distal member toward an m direction midway between the x direction and the y direction which would involve approximately equal portions of pitch and yaw. This would similarly be the case for tipping toward an m', m" or m'" direction as shown in FIG. 5.

Figure 6A:
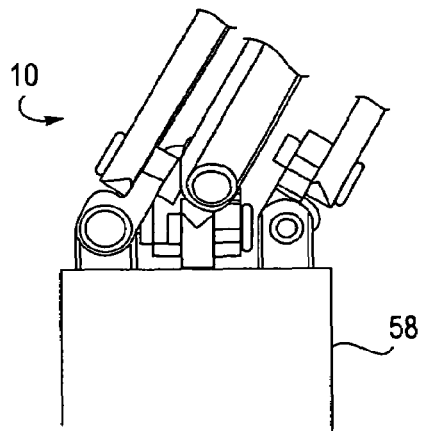
FIGS. 6A-6F illustrate three different embodiments of the wrist mechanism of the present invention.
Figure 6B:
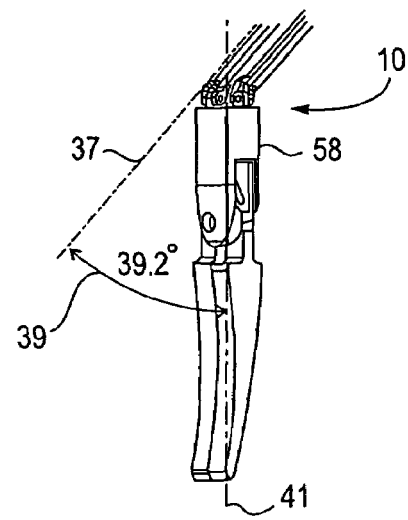
Figure 6C:
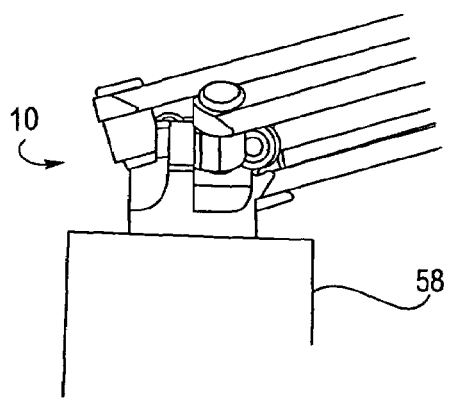
Figure 6D:
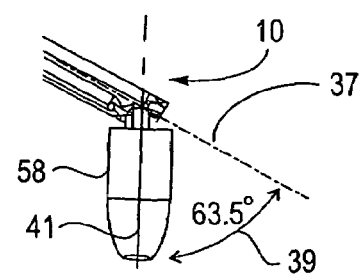
Figure 6E:
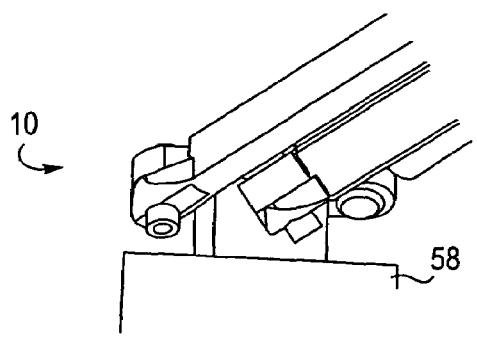
Figure 6F:
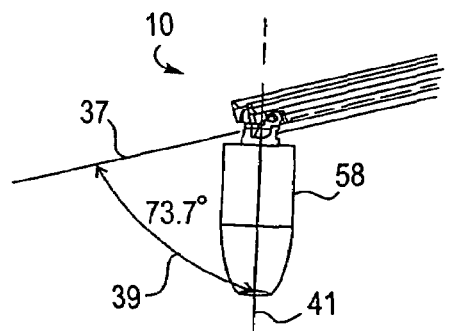

In these positions, different variations in the wrist mechanism 10 design allow movement of the distal member through different ranges of angles. For example, three different embodiments of the wrist mechanism 10 are shown in FIGS. 6A-6F wherein each wrist mechanism 10 design provides a different range of motion in this most challenging position. FIG. 6A is an illustration of a first main embodiment of the wrist mechanism 10 which allows movement in the approximate range of ±40 degrees, as illustrated in corresponding FIG. 6B. In FIG. 6B, a plurality of rods are shown wherein a first rod and a second rod are extended generally along an axial direction 37 which tips the clevis 58 through a combination of a first angle and a second angle (forming a compound angle 39) so that the clevis 58 faces an articulated direction 41. In this example, the angle 39 is approximately 39.2 degrees. This wrist mechanism embodiment was introduced above and will be further described herein below. FIG. 6C is an illustration of a second main embodiment of the wrist mechanism 10 which allows movement in the approximate range of ±64 degrees, as illustrated in corresponding FIG. 6D. Again, a plurality of rods are shown wherein a first rod and a second rod are extended generally along an axial direction 37 which tips the clevis 58 through a first angle and a second angle (forming a compound angle 39) so that the clevis 58 faces a articulated direction 41. In this example, the angle 39 is approximately 63.5 degrees. FIG. 6E is an illustration of a third main embodiment of the wrist mechanism 10 which allows movement in the approximate range of ±74 degrees, as illustrated in corresponding FIG. 6F. Likewise, a plurality of rods are shown wherein a first rod and a second rod are extended generally along an axial direction 37 which tips the clevis 58 through a first angle and a second angle (forming a compound angle 39) so that the clevis 58 faces a articulated direction 41. In this example, the angle 39 is approximately 73.7 degrees.

Figure 7:
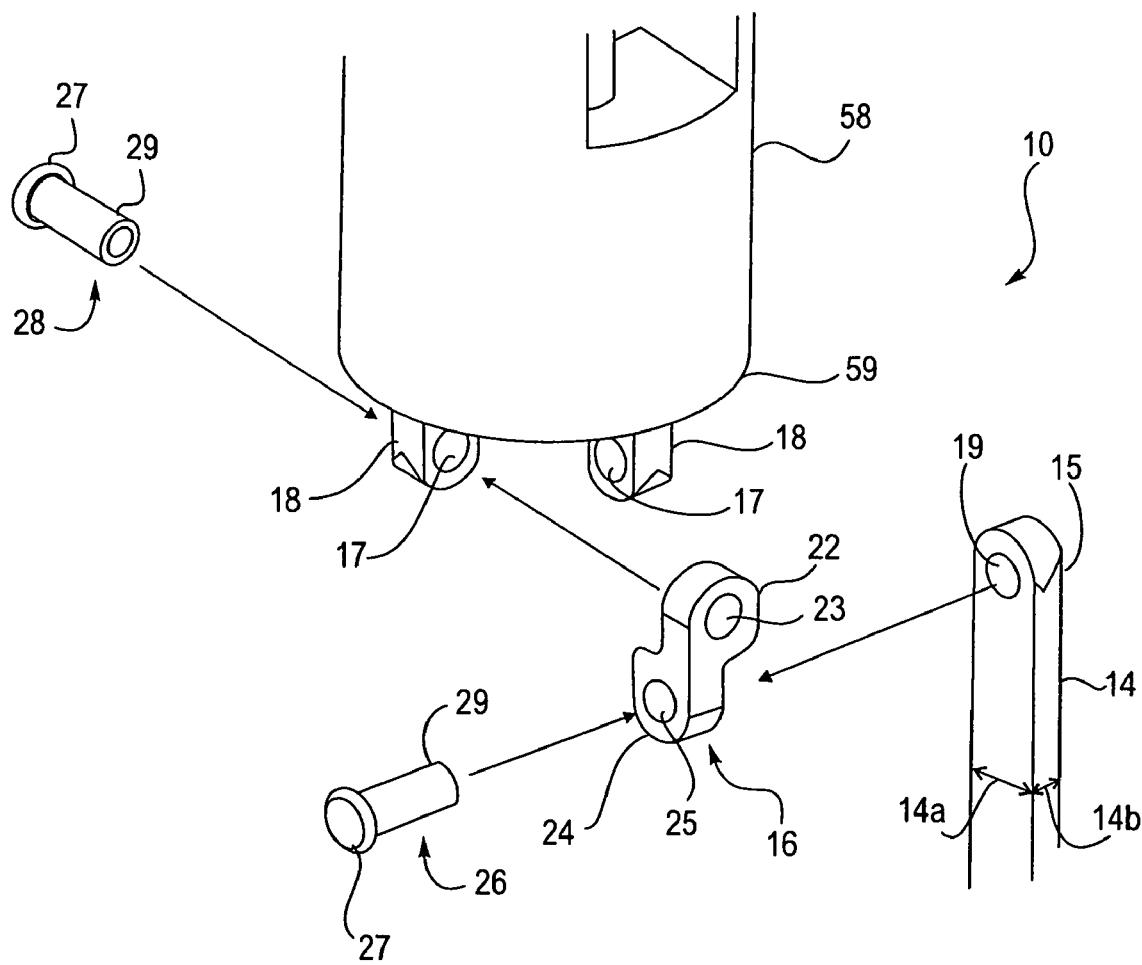
FIG. 7 illustrates assemblage of the first main embodiment of the wrist mechanism.
Figure 8:
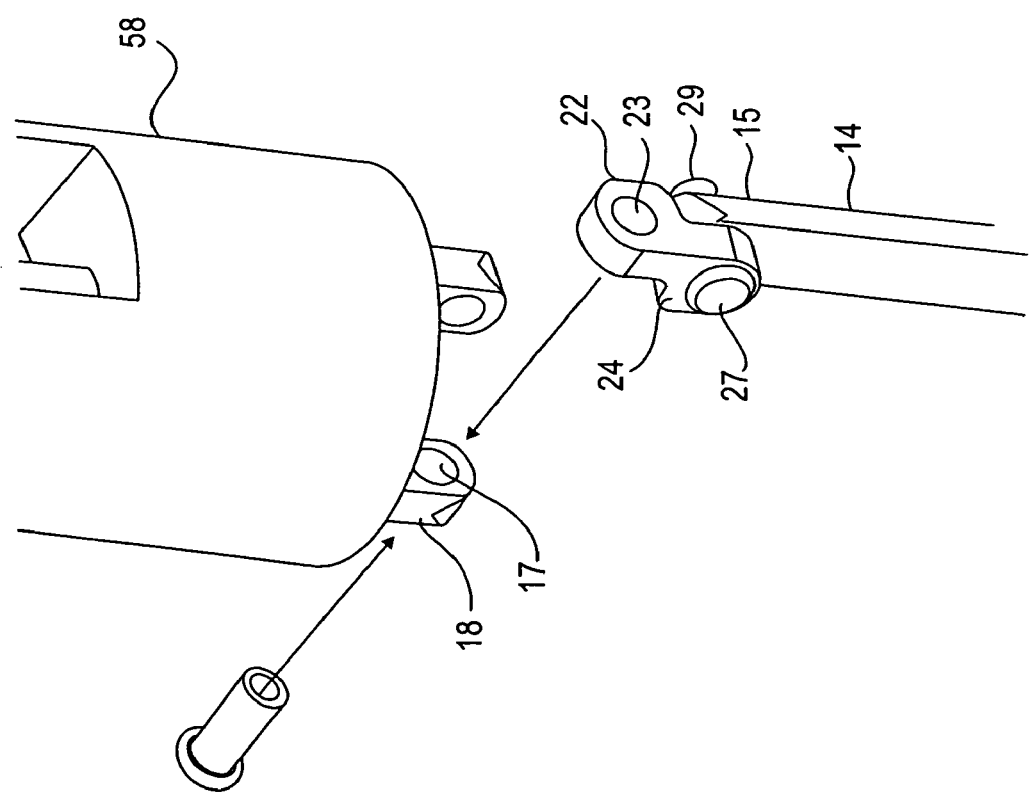

The three different main embodiments of FIGS. 6A-6F will now be more fully described and illustrated. The wrist mechanism 10 of the first main embodiment is illustrated in FIGS. 7-10, 11A-11B, 12, 13 and provides motion in the approximate range of ±40 degrees, under the conditions described above. Referring to FIG. 7, the distal member is in the form of a distal clevis 58 which has a plurality of feet 18 with apertures 17. In this view, two feet 18 are visible, however four feet 18 are present in this embodiment positioned symmetrically around a base 59 of the distal clevis 58, as partially shown. Each rod 14 is connected with one of the feet 18 by an orthogonal linkage assembly. In this embodiment, the orthogonal linkage assembly comprises an orthogonal linkage 16 which has a first link portion 22 with a first aperture 23 and a second link portion 24 with a second aperture 25, wherein the first link portion 22 and second link portion 24 lie in perpendicular planes. Consequently, the apertures 23, 25 face directions which are 90 degrees apart. A rod 14 is connected to the second link portion 24 by inserting fastener 26 through second aperture 25 and through aperture 19 located near the distal end 15 of the rod 14. As shown, aperture 19 passes through the wide side 14a of the rod 14. The fastener 26 may be of any suitable type, for example the fastener 26 may include a head 27 and a body 29 as shown. In this case, the body 29 is inserted through the appropriate apertures. Once inserted, the fastener 26 is then held in place by altering the body 29, such as by swaging, to create a flange, lip, hook or crimp. Thus, the second link portion 24 and distal end 15 of the rod 14 may be held together between the head 27 and the swaged end of the body 29. This allows free rotation of the rod 14 in the plane of the second link portion 24. Such joining of the second link portion 24 and distal end 15 of the rod 14 is illustrated in FIG. 8.

Figure 9:
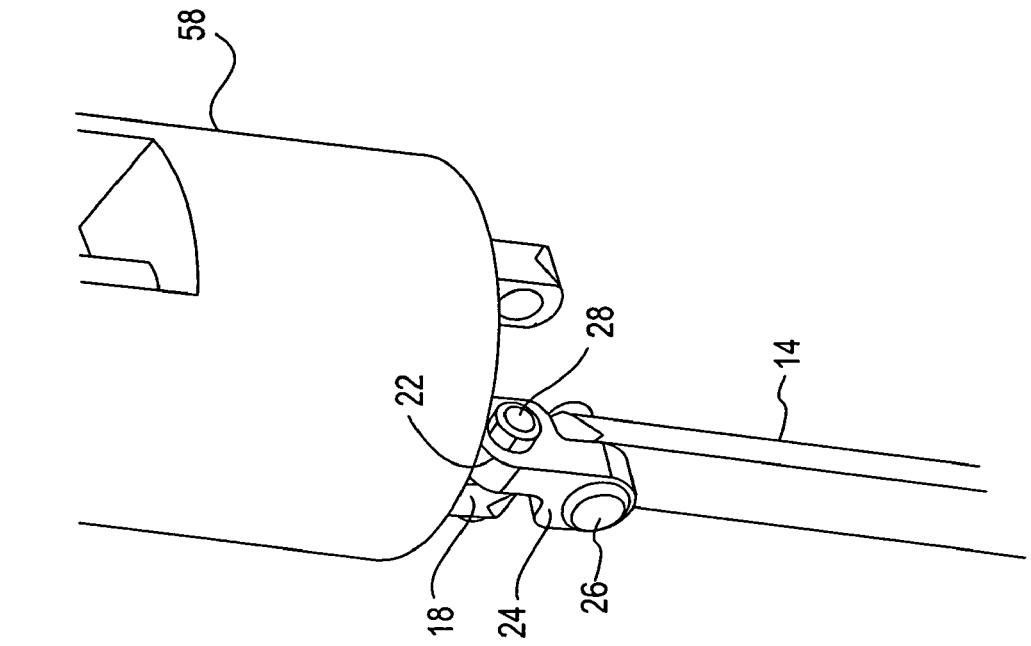
FIGS. 8-9 illustrate joining of a rod with an orthogonal linkage and then joining of the linkage with a foot on the distal clevis.

Similarly, the first link portion 22 is connected with one of the feet 18 by inserting fastener 28 through aperture 17 of foot 18 and through first aperture 23 of the first link portion 22. Again, once inserted, fastener 28 can be held in place by altering the body 29, such as by swaging. Thus, the first link portion 22 and foot 18 may be held together between the head 27 and the swaged end of the body 29. This allows free rotation of the first link portion 22 in the plane of the foot 18. Such joining of the first link portion 22 and foot 18 is illustrated in FIG. 9. Due to the shape of the orthogonal linkage 16 and the perpendicular orientation of the apertures 23, 25, the foot 18 is able to be translated in the plane of second link portion 24 or wide side 14a of the rod 14, offset from aperture 19, while being rotated in a plane perpendicular to the plane of second link portion 24, or parallel to the narrow side 14b of the rod 14. Consequently, the distal clevis 58 attached to the foot 18 may be tipped to various degrees along two axes simultaneously.

Figure 10:
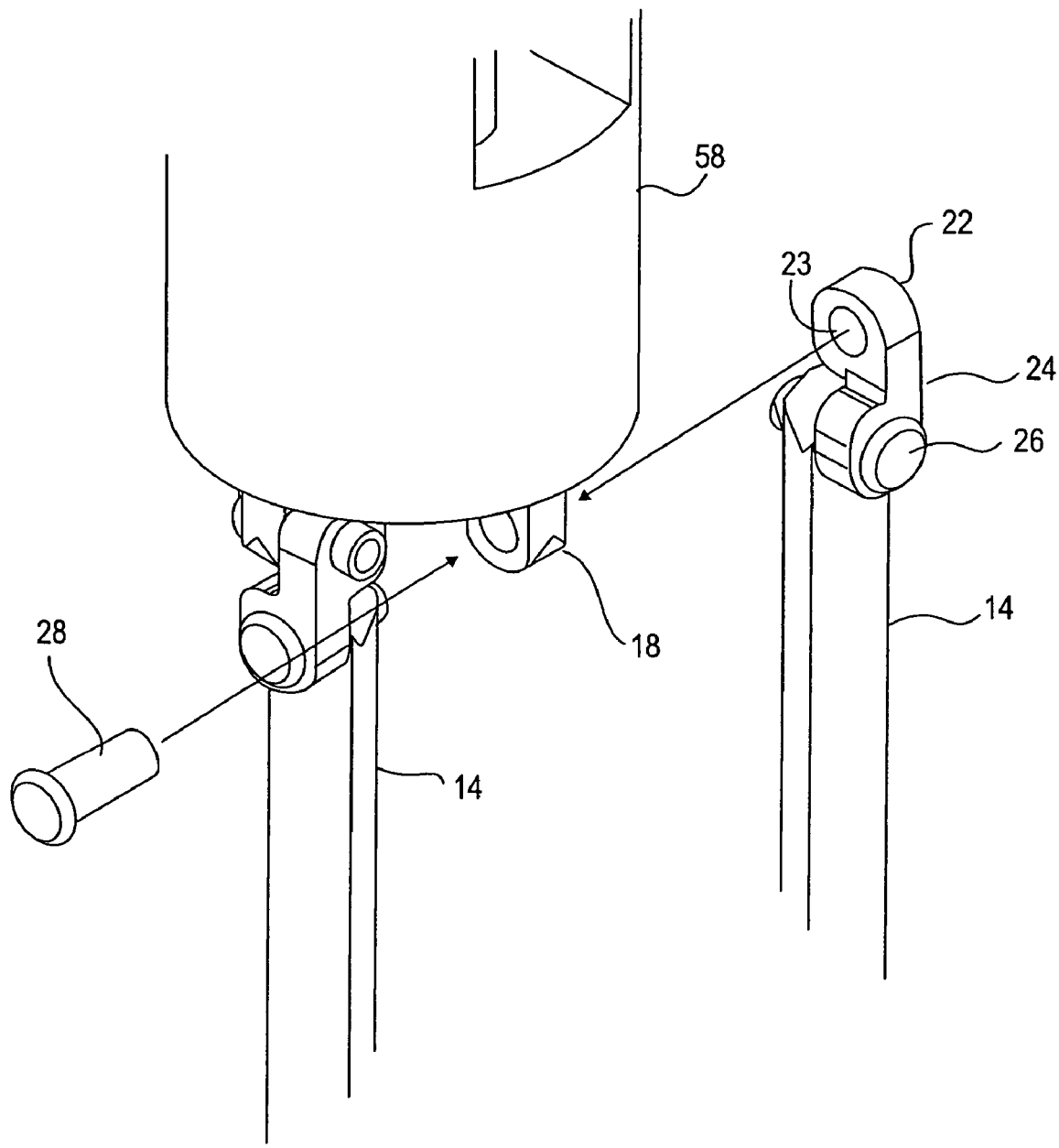
FIG. 10 illustrates joining of additional rods to the distal clevis.
Figure 11A:
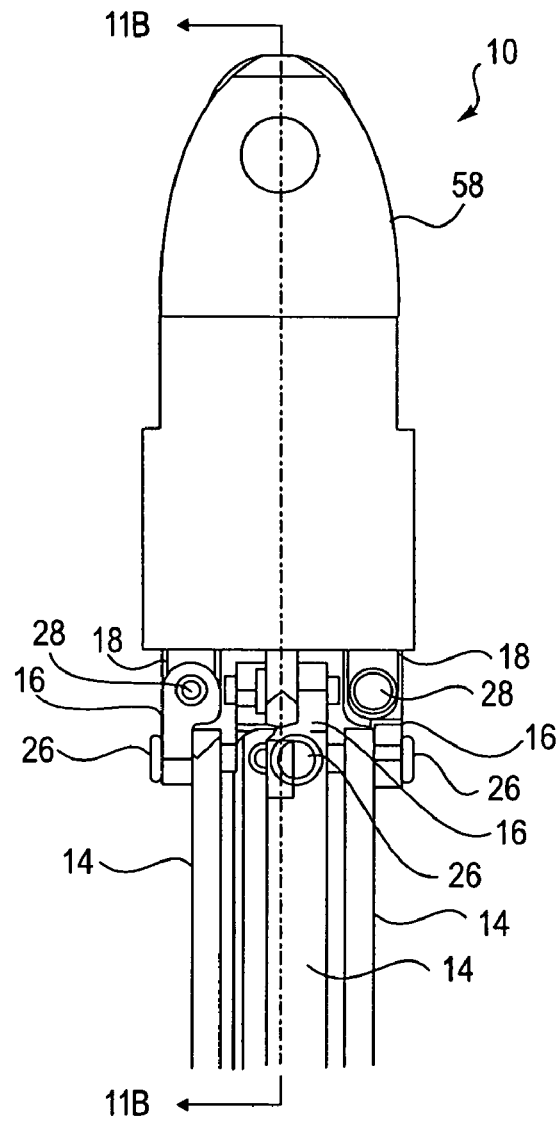
FIG. 11A illustrates the first main embodiment of the wrist mechanism wherein four rods are attached.
Figure 11B:
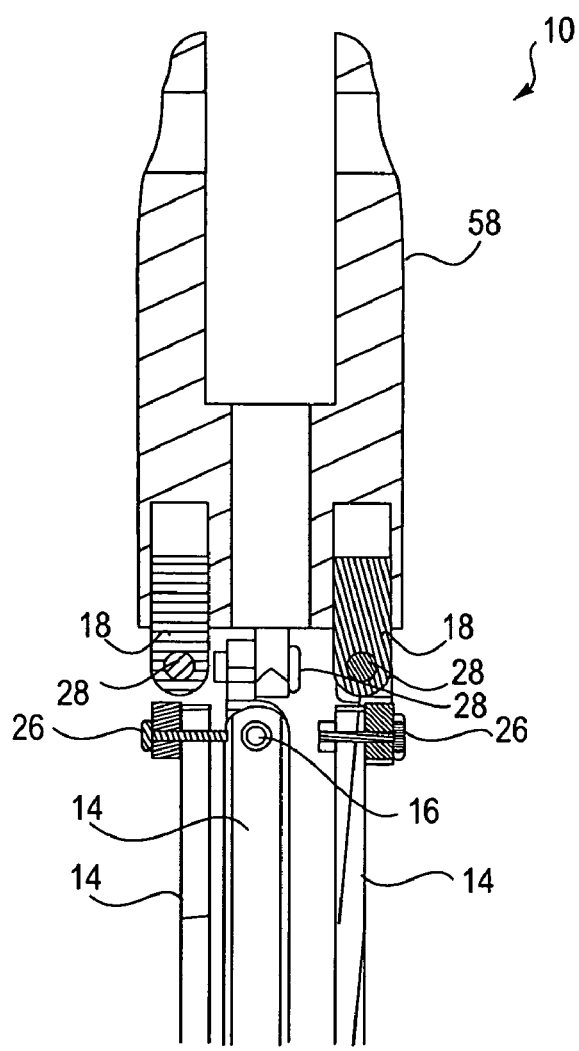
FIG. 11B is a cross-sectional view of FIG. 11A.

As shown in FIG. 10, each of the four rods 14 are connected with a corresponding foot 18 as described above. FIG. 11A illustrates the wrist mechanism 10 wherein all four rods 14 are attached to the feet 18 of the distal clevis 58. FIG. 11B is a cross-sectional view of FIG. 11A. When four rods 14 are present, advancement of one rod tips the distal clevis 58 to face away from the advanced rod. In some embodiments, this simultaneously retracts the rod attached to the distal clevis 58 in the diametrically opposite position. When a rod adjacent to the advanced rod is advanced, the distal clevis 58 is tipped to face away from the newly advanced rod simultaneously retracting the diametrically opposite rod. By varying which rods are advanced and the amount by which they are advanced, the distal clevis can be tipped through a continuous series of angles.

The wrist mechanism 110 of the second main embodiment is illustrated in FIGS. 12-16, 17A-17B, 18, 19, and provides motion in the approximate range of ±64 degrees, under the conditions described above. In this embodiment, the distal clevis 158 is comprised of a first clevis half 102 and a second clevis half 104 which are then mated by a clevis mater 106 and joined with a clevis tip 108. This arrangement allows ease of assembly, reduction of parts and an increased range of motion.

Figure 12:
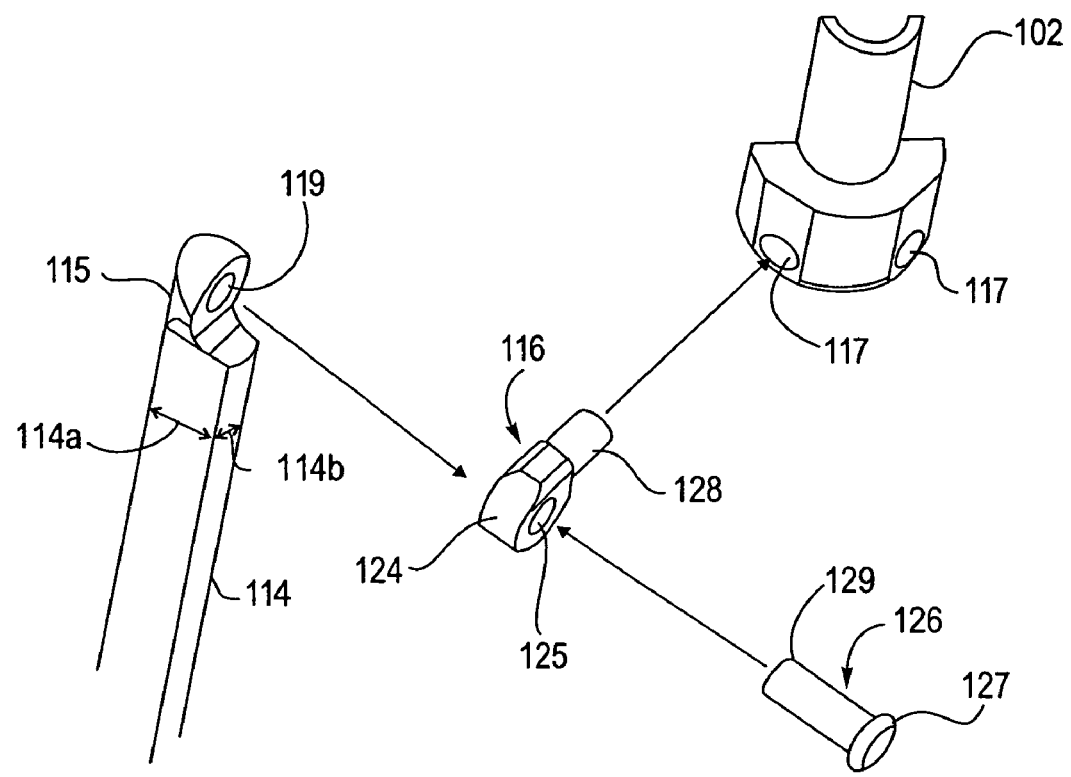
FIG. 12 illustrates assemblage of the second main embodiment of the wrist mechanism.
Figure 13:
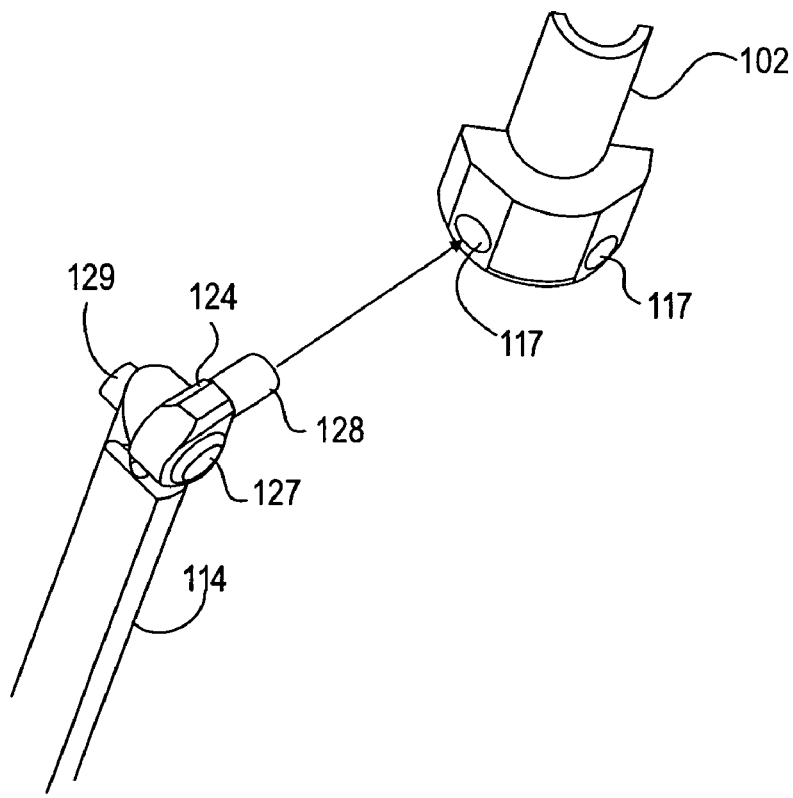
FIG. 13 illustrates joining of a rod with a linkage fastener and for later joining with a distal clevis half.

Referring to FIG. 12, the first clevis half 102 is illustrated. Rather than having feet as in the first main embodiment, apertures 117 are formed directly in the first clevis half 102. The rod 114 is then attached to the first clevis half 102 with the use of linkage fastener 116. The linkage fastener 116 comprises a link base portion 124 with an aperture 125 and a fastening end portion 128 which extends in the same plane as the link base portion 124. A rod 114 is connected to the link base portion 124 by inserting fastener 126 through aperture 125 and through aperture 119 located near the distal end 115 of the rod 114. As shown, aperture 119 passes through the narrow side 114b of the rod 114. The fastener 126 may be of any suitable type, for example the fastener 126 is shown to include a head 127 and a body 129. In this case, the body 129 is inserted through the appropriate apertures. Once inserted, the fastener 126 is then held in place by altering the body 129, such as by swaging, to create a flange, lip, hook or crimp. Thus, the link base portion 124 and distal end 115 of the rod 114 may be held together between the head 127 and the swaged end of the body 129. This allows free rotation of the rod 114 in the plane of the link base portion 124. Such joining of the link base portion 124 and distal end 115 of the rod 114 is illustrated in FIG. 13.

The linkage fastener 116 is then connected with first clevis half 102 by inserting fastening end portion 128 through aperture 117. Once inserted, the linkage fastener 116 can be held in place by altering the fastening end portion 128, such as by swaging, to create a flange, lip, hook or crimp on the inside of the first clevis half 102. Thus, the first clevis half 102 may be held between the link base portion 124 and the swaged end of the fastening end portion 128. This allows free rotation of the first clevis half 102 in the plane perpendicular to the link base portion 124. Due to the shape of the linkage fastener 116 and the orientation of the apertures 119, 125, 117, the first clevis half 102 is able to be translated in the plane of link base portion 124 or narrow side 114b of the rod 114, offset from aperture 119, while being rotated in a plane perpendicular to the plane of link base portion 124, or parallel to the wide side 114a of the rod 114. Consequently, the first clevis half 102 attached may be tipped to various degrees along two axes simultaneously.

Figure 14:
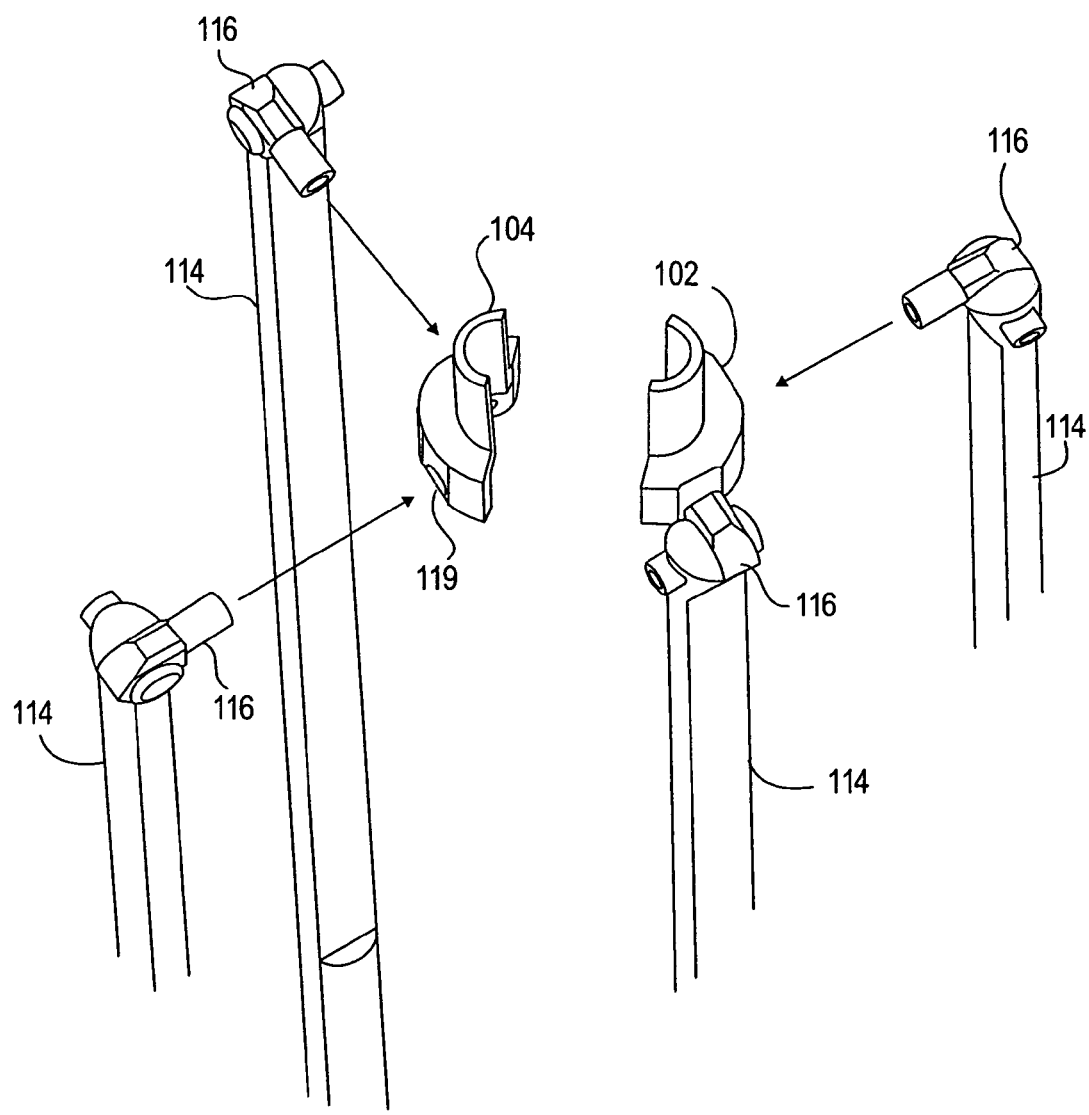
FIG. 14 illustrates joining rods with corresponding apertures on the first and second clevis halves with the use of linkage fasteners.
Figure 15:
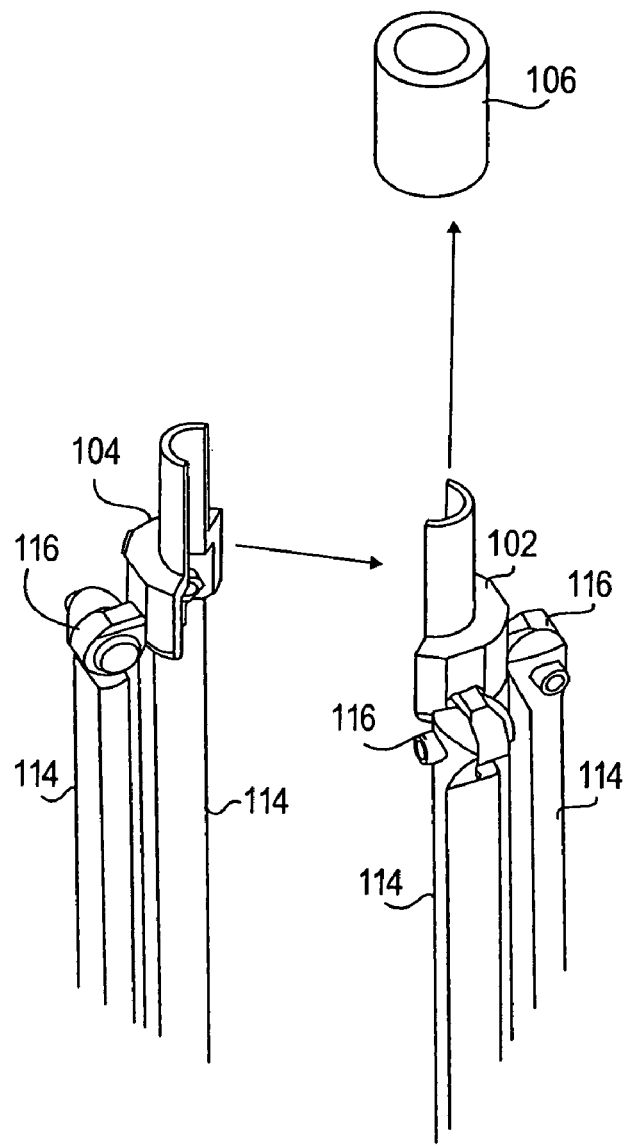
FIGS. 15-16 show mating of the clevis halves and joining with a clevis tip.
Figure 16:
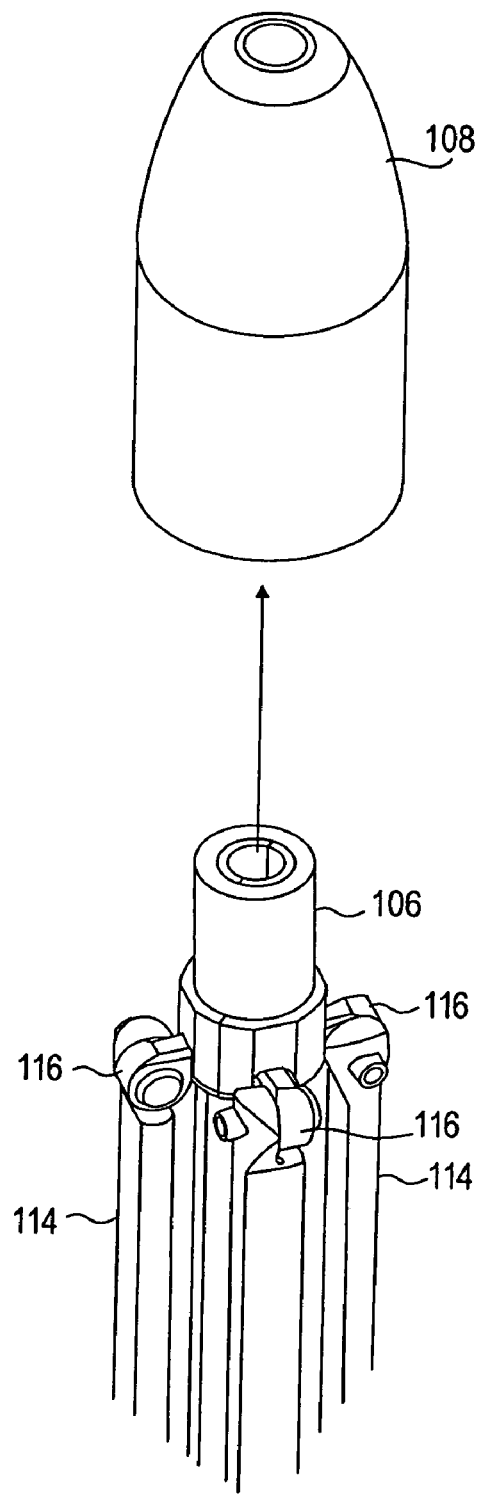

As shown in FIG. 14, rods 114 are connected with corresponding apertures 119 on the first clevis half 102 and the second clevis half 104 with the use of linkage fasteners 116 as described above. In this embodiment, two rods 114 are attached to each half 102, 104 for a total of four symmetrically placed rods. Again, it may be appreciated that any number of rods 114 may be used and attached to the clevis halves 102, 103 in any arrangement. As shown in FIG. 15, the clevis halves 102, 103 are then mated by insertion into the clevis mater 106. The clevis mater 106 may be a ring, as shown, wherein the halves 102, 103 are press fit within. Referring now to FIG. 16, the clevis mater 106 is then joined with the clevis tip 108, typically by a threaded fit or press fit.

Figure 17A:
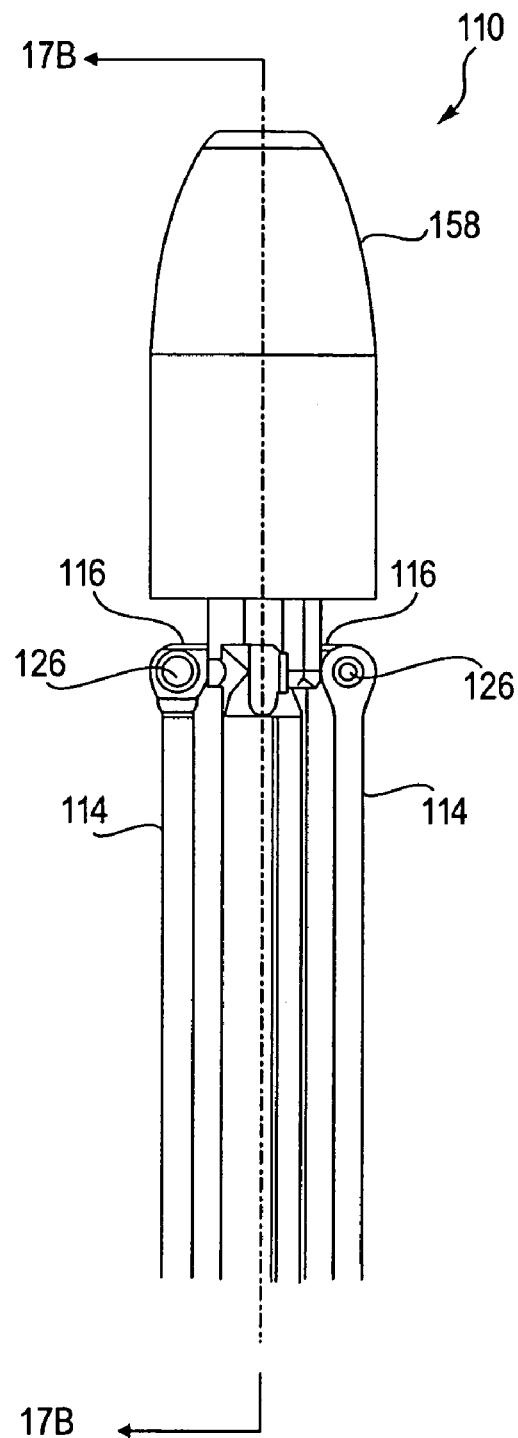
FIG. 17A illustrates the second main embodiment of the wrist mechanism wherein four rods are attached.
Figure 17B:
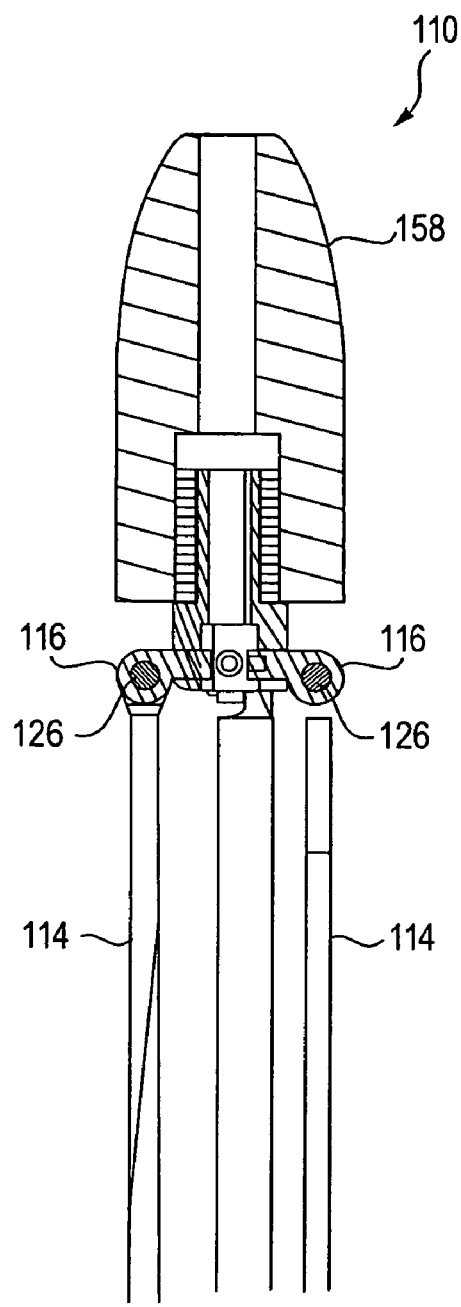
FIG. 17B is a cross-sectional view of FIG. 17A.
Figures 18, 19:
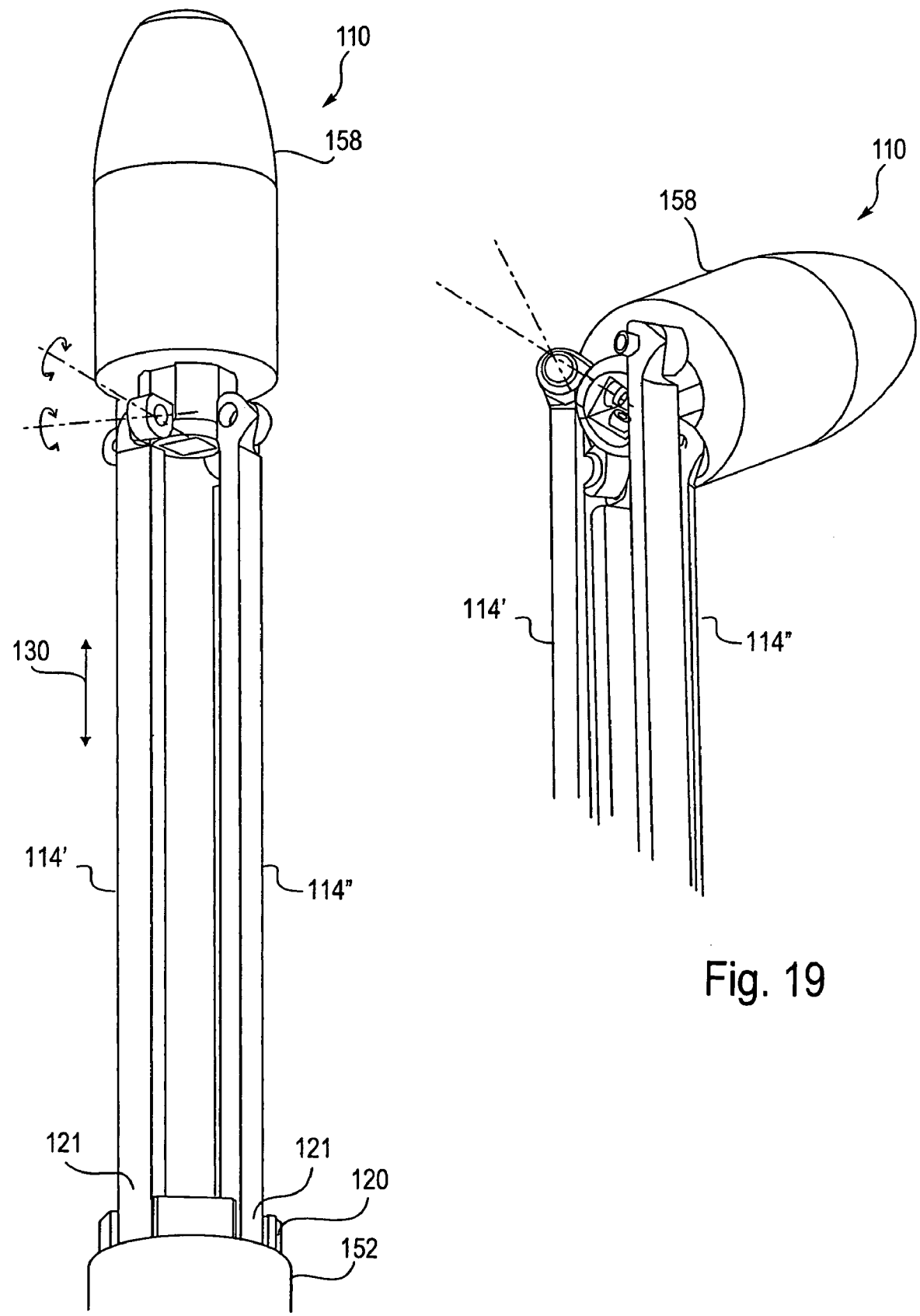
FIG. 18 is a perspective view of an embodiment of the wrist mechanism showing rods inserted through a guide tube.
FIG. 19 illustrates tipping of the distal clevis in response to advancement and/or retraction of one or more rods.

FIG. 17A illustrates the wrist mechanism 110 wherein all four rods 114 are attached to distal clevis 158. FIG. 17B is a cross-sectional view of FIG. 17A. FIG. 18 provides a perspective view of the wrist mechanism 110 showing the rods 114 inserted through guide tube 120 in shaft 152 of the tool 50. The guide tube 120 includes guide slots 121 through which the rods 114 pass to hold rods 114 in the desired orientation. Advancement (indicated by arrow 130) of one rod 114' tips the distal clevis 158 to face away from the advanced rod 114', as illustrated in FIG. 19. In some embodiments, this simultaneously retracts the rod 114" attached to the distal clevis 158 in the diametrically opposite position. When a rod adjacent to the advanced rod is advanced, the distal clevis 158 is tipped to face away from the newly advanced rod simultaneously retracting the diametrically opposite rod. By varying which rods are advanced and the amount by which they are advanced, the distal clevis can be tipped through a continuous series of angles.

Figure 20:
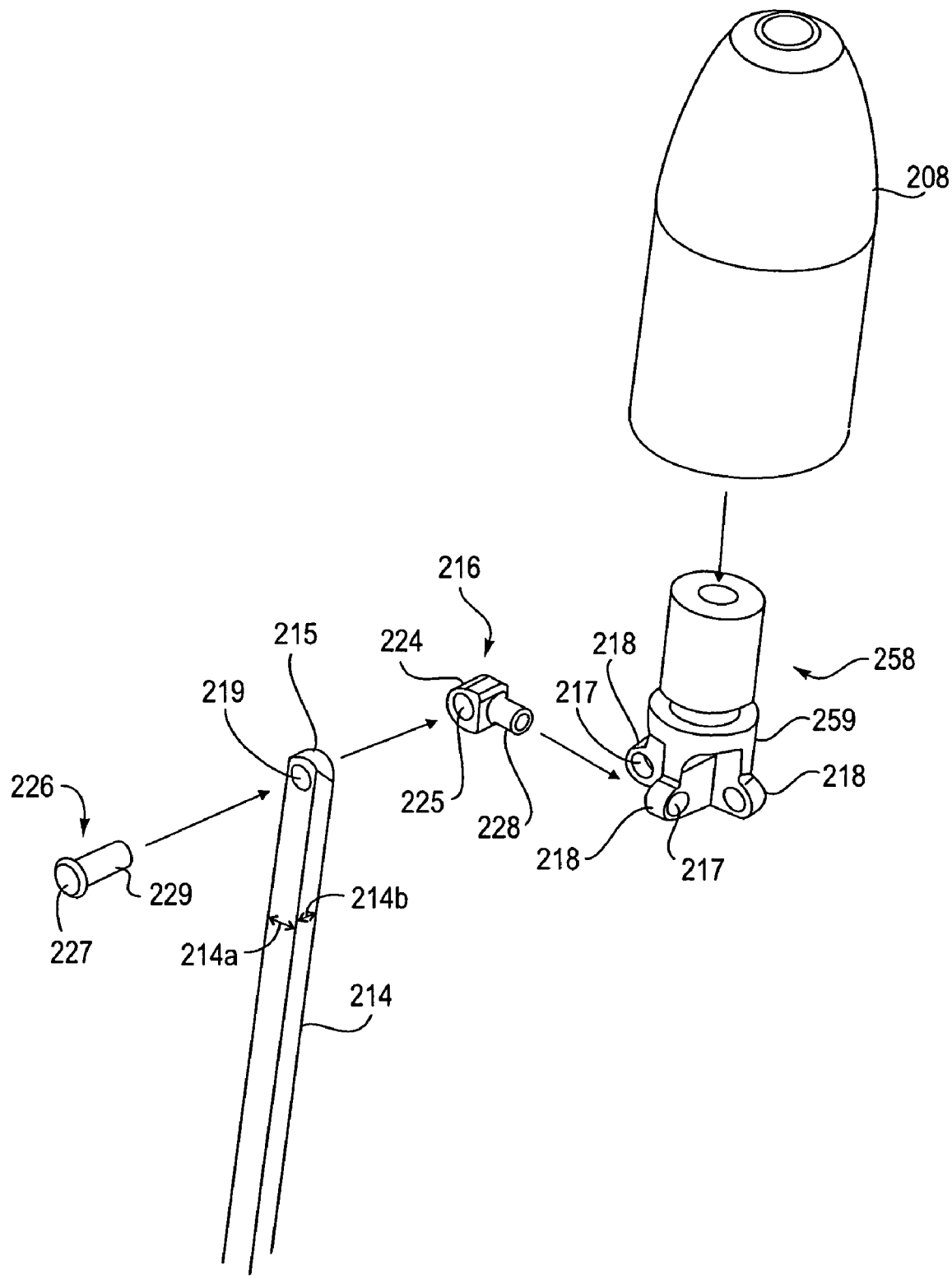
FIG. 20 illustrates assemblage of the third main embodiment of the wrist mechanism.

The wrist mechanism 210 of the third main embodiment is illustrated in FIGS. 20-22, 23A-23B, 24, and provides motion in the approximate range of ±74 degrees, under the conditions described above. Referring to FIG. 20, the distal member is in the form of a distal clevis 258, which has a plurality of feet 218 with apertures 217 and a clevis tip 208. In this view, three feet 218 are visible, however four feet 218 are present in this embodiment positioned symmetrically around a base 259 of the distal clevis 258, as partially shown. Each rod 214 is connected with one of the feet 218 by an linkage fastener 216. This arrangement allows ease of assembly, reduction of parts and an increased range of motion.

Figure 21:
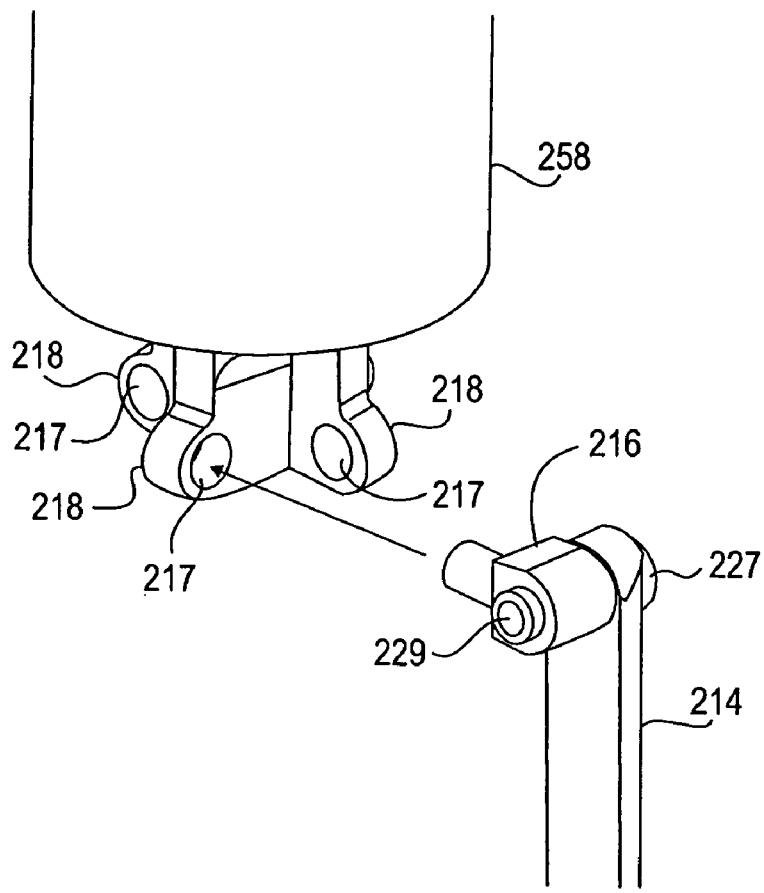
FIGS. 21-22 illustrate joining of a rod with an linkage fastener and then joining linkage fastener with a foot on the distal clevis.

The linkage fastener 216 comprises a link base portion 224 with an aperture 225 and a fastening end portion 228 which extends in the same plane as the link base portion 224. A rod 214 is connected to the link base portion 224 by inserting fastener 226 through aperture 219, located near the distal end 215 of the rod 214 and passes through the wide side 214b of the rod 214, and through aperture 225. The fastener 226 may be of any suitable type, for example the fastener 226 is shown to include a head 227 and a body 229. In this case, the body 229 is inserted through the appropriate apertures. Once inserted, the fastener 226 is then held in place by altering the body 229, such as by swaging, to create a flange, lip, hook or crimp. Thus, the link base portion 224 and distal end 215 of the rod 214 may be held together between the head 227 and the swaged end of the body 229. This allows free rotation of the rod 214 in the plane of the link base portion 224. Such joining of the link base portion 224 and distal end 215 of the rod 214 is illustrated in FIG. 21.

Figure 22:
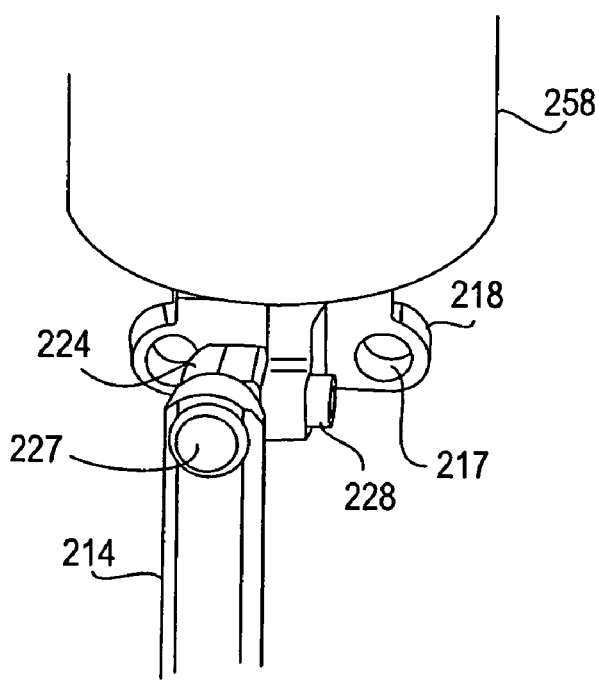

The linkage fastener 216 is then connected with the distal clevis 258 by inserting fastening end portion 228 through aperture 117, as illustrated in FIG. 22. Once inserted, the linkage fastener 216 can be held in place by altering the fastening end portion 228, such as by swaging. Thus, the foot 218 may be held between the link base portion 224 and the swaged end of the fastening end portion 228. This allows free rotation of the foot 218 in the plane perpendicular to the link base portion 224. Due to the shape of the linkage fastener 216 and the orientation of the apertures 219, 225, 217, the foot 218 is able to be translated in the plane of the link base portion 224 or wide side 214a of the rod 214, offset from aperture 219, while being rotated in a plane perpendicular to the plane of link base portion 224, or parallel to the narrow side 214b of the rod 214. Consequently, the attached distal clevis 258 may be tipped to various degrees along two axes simultaneously.

Figure 23A:
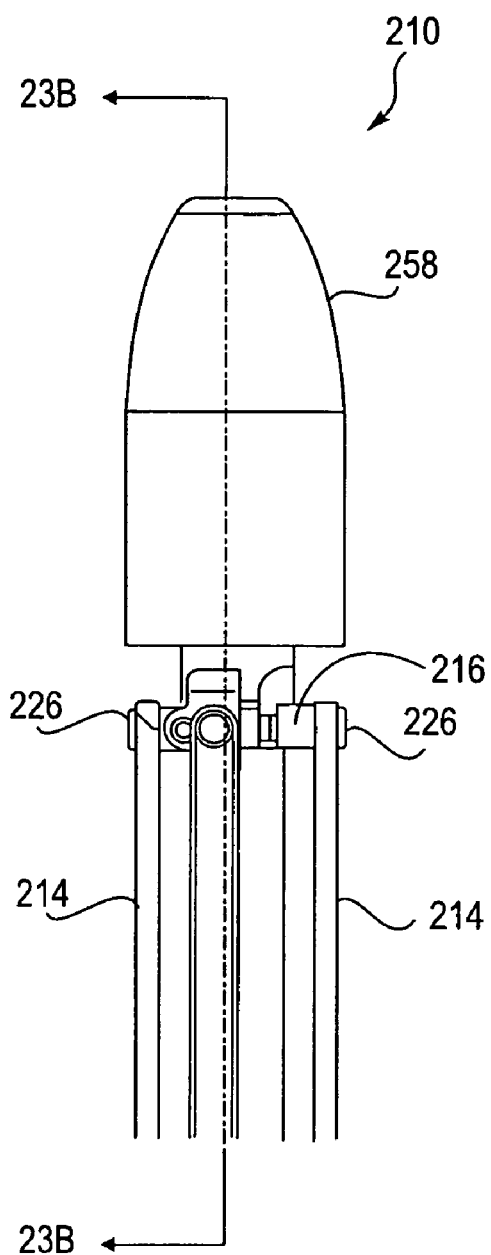
FIG. 23A illustrates the third main embodiment of the wrist mechanism wherein four rods are attached.
Figure 23B:
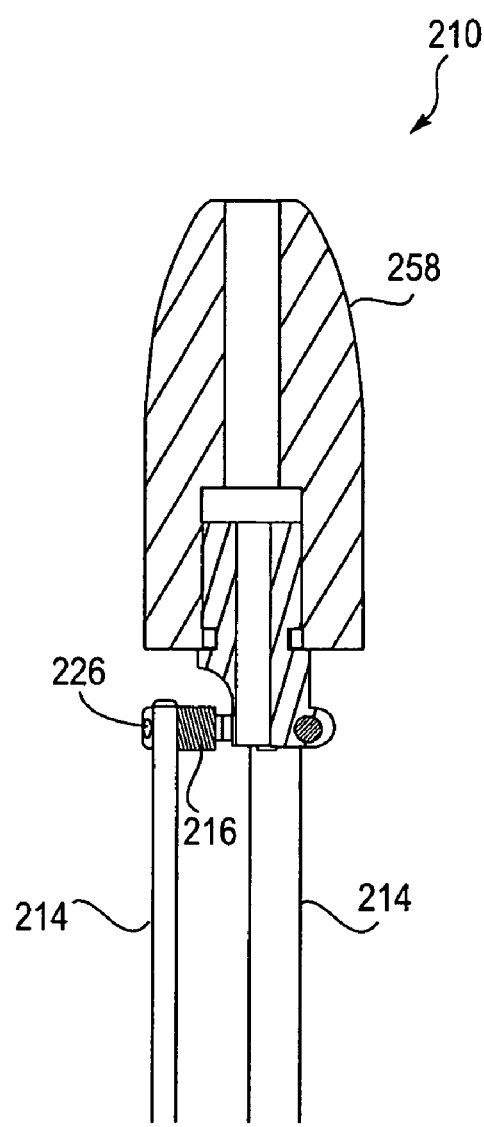
FIG. 23B is a cross-sectional view of FIG. 23A.
Figure 24:
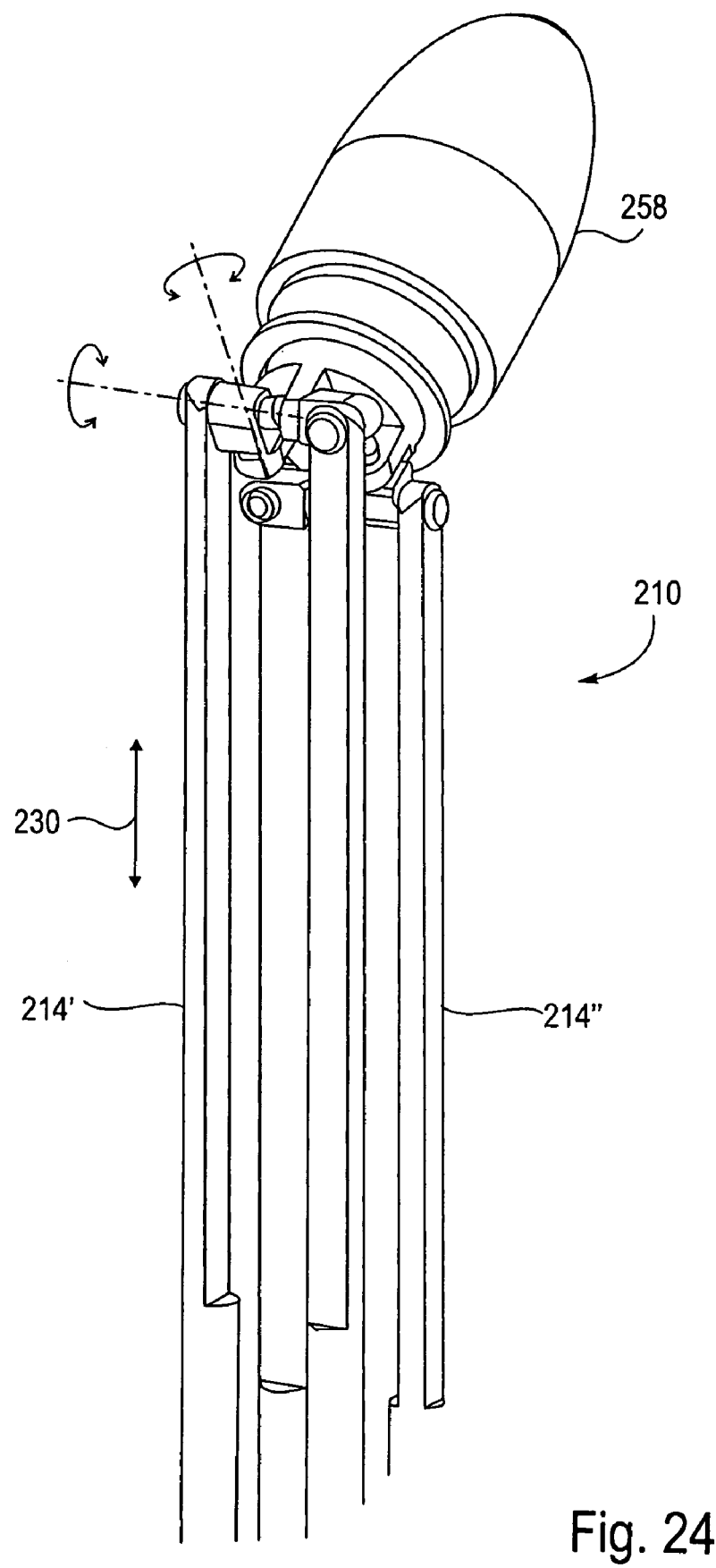
FIG. 24 illustrates tipping of the distal clevis in response to advancement and/or retraction of one or more rods.

FIG. 23A illustrates the wrist mechanism 210 wherein all four rods 214 are attached to distal clevis 258. FIG. 23B is a cross-sectional view of FIG. 23A. FIG. 24 provides a perspective view of the wrist mechanism 210. Advancement (indicated by arrow 230) of one rod 214' tips the distal clevis 258 to face away from the advanced rod 214'. In some embodiments, this simultaneously retracts the rod 214" attached to the distal clevis 258 in the diametrically opposite position. When a rod adjacent to the advanced rod is advanced, the distal clevis 258 is tipped to face away from the newly advanced rod simultaneously retracting the diametrically opposite rod. By varying which rods are advanced and the amount by which they are advanced, the distal clevis can be tipped through a continuous series of angles.

Figure 27:
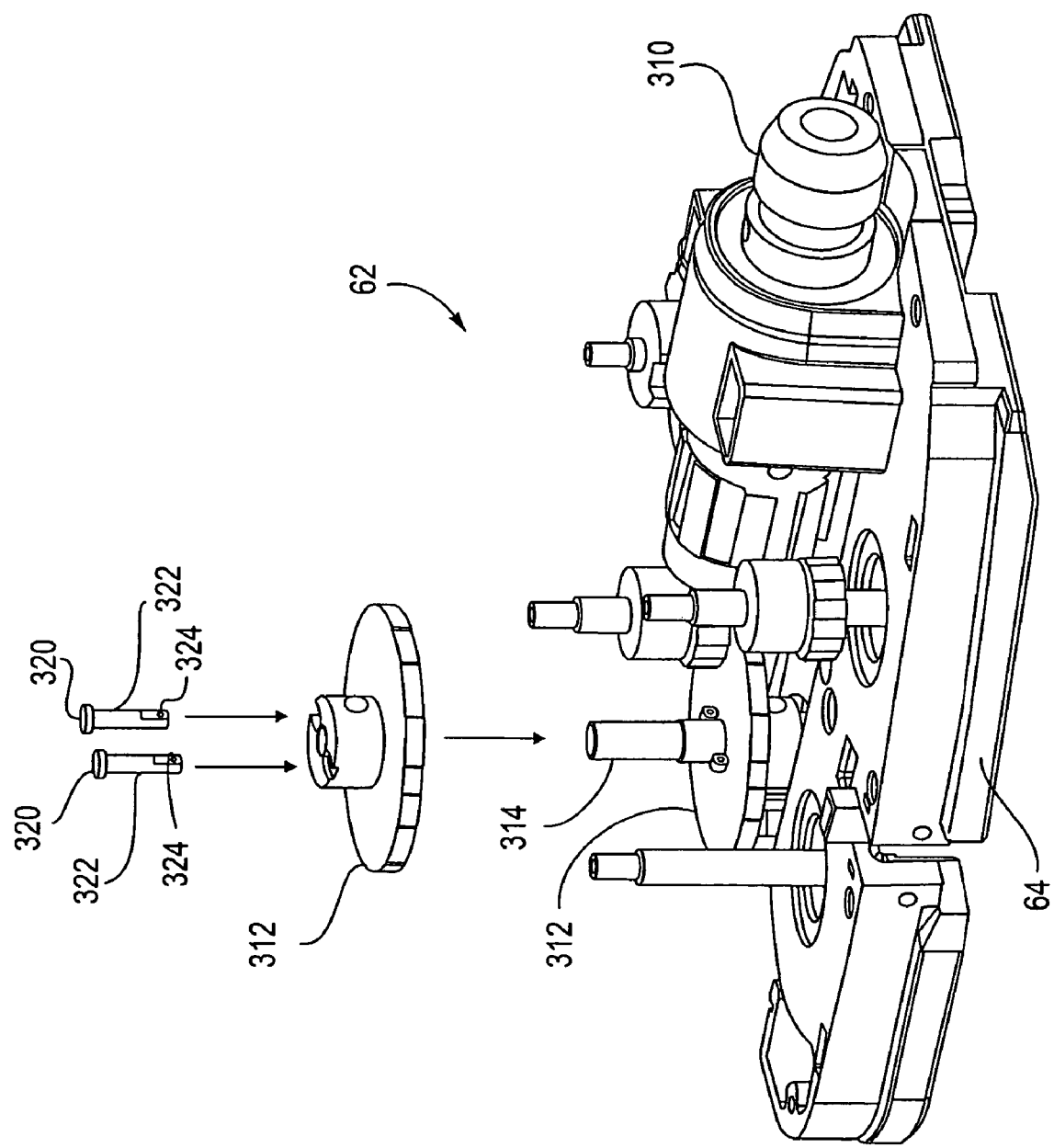
FIG. 27 illustrates additional features of the tool base, including rotational actuation members.

Actuation of any of the wrist mechanism embodiments described above is achieved with the use of the tool base 62 schematically depicted in FIG. 1. As shown, the proximal end 54 of the shaft 52 is coupled to the tool base 62. Rods extend through the shaft 52 from the wrist mechanism 10 to the tool base 62 wherein the rods are manipulated to actuate the wrist mechanism. For ease of manipulation, each rod 300 is joined with a cable or wire 302, as illustrated in FIG. 25. The wire 302 has a smaller diameter than the rod 300 and mates concentrically with the center 304 of the rod 300. Referring to FIG. 26, the wire/rod assembly 305 is then inserted through a roll pulley 310 within the tool base 62. The tool base 62 further includes rotational actuation member, such as a sector gear 312, mounted on a sector pivot pin 314, as shown in FIG. 27. Inserted into each sector gear 312 are two pivot pins 320, one on each side of the gear 312. Each pivot pin 320 has a flat surface 322 and a crosshole 324. When inserted into a sector gear 312, the pivot pins 320 can freely rotate to allow maximum roll angle articulation.

Figure 28:
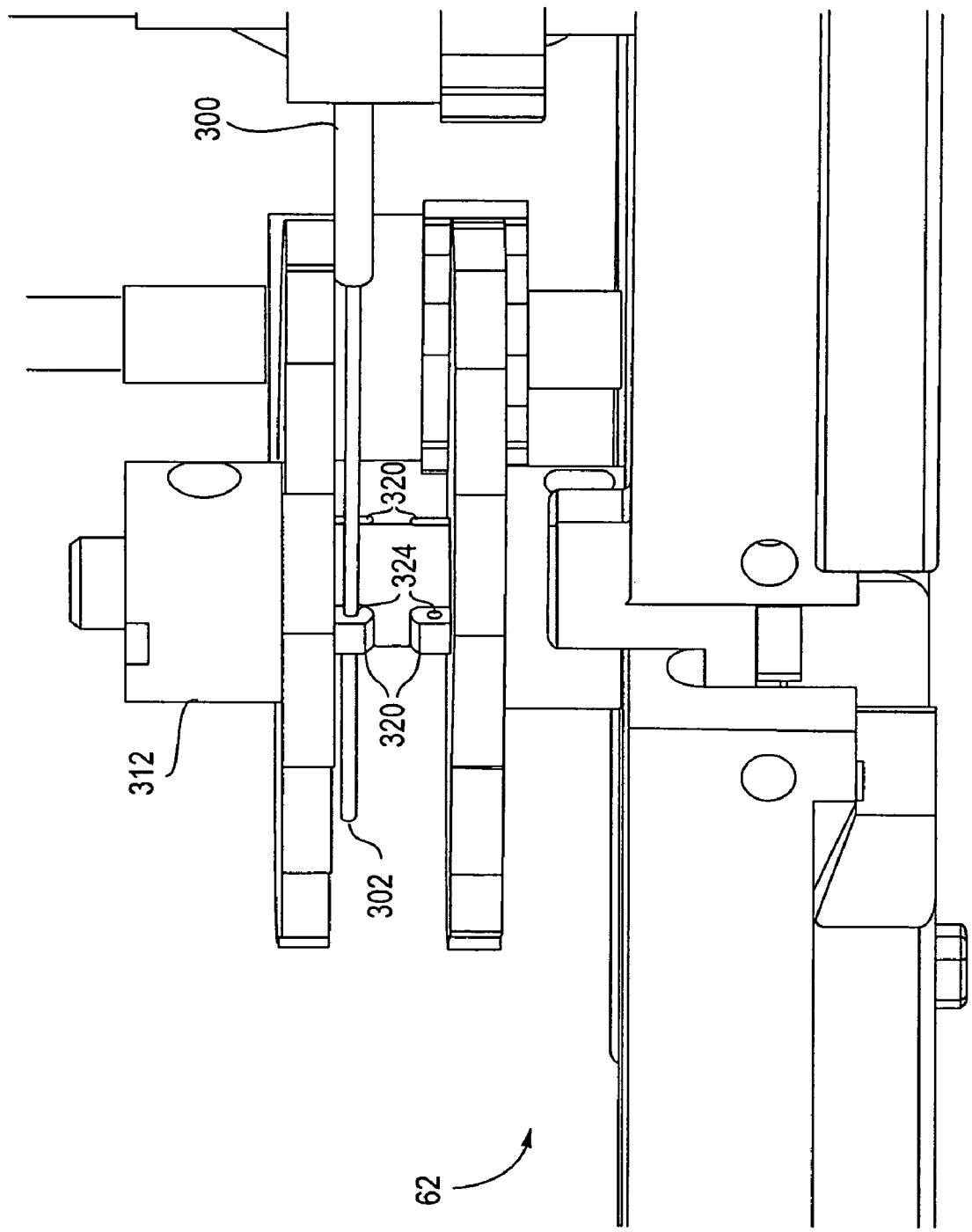
FIG. 28 is a side view illustrating insertion of the wire through a crosshole in a pivot pin which is mounted in a sector gear.
Figure 29:
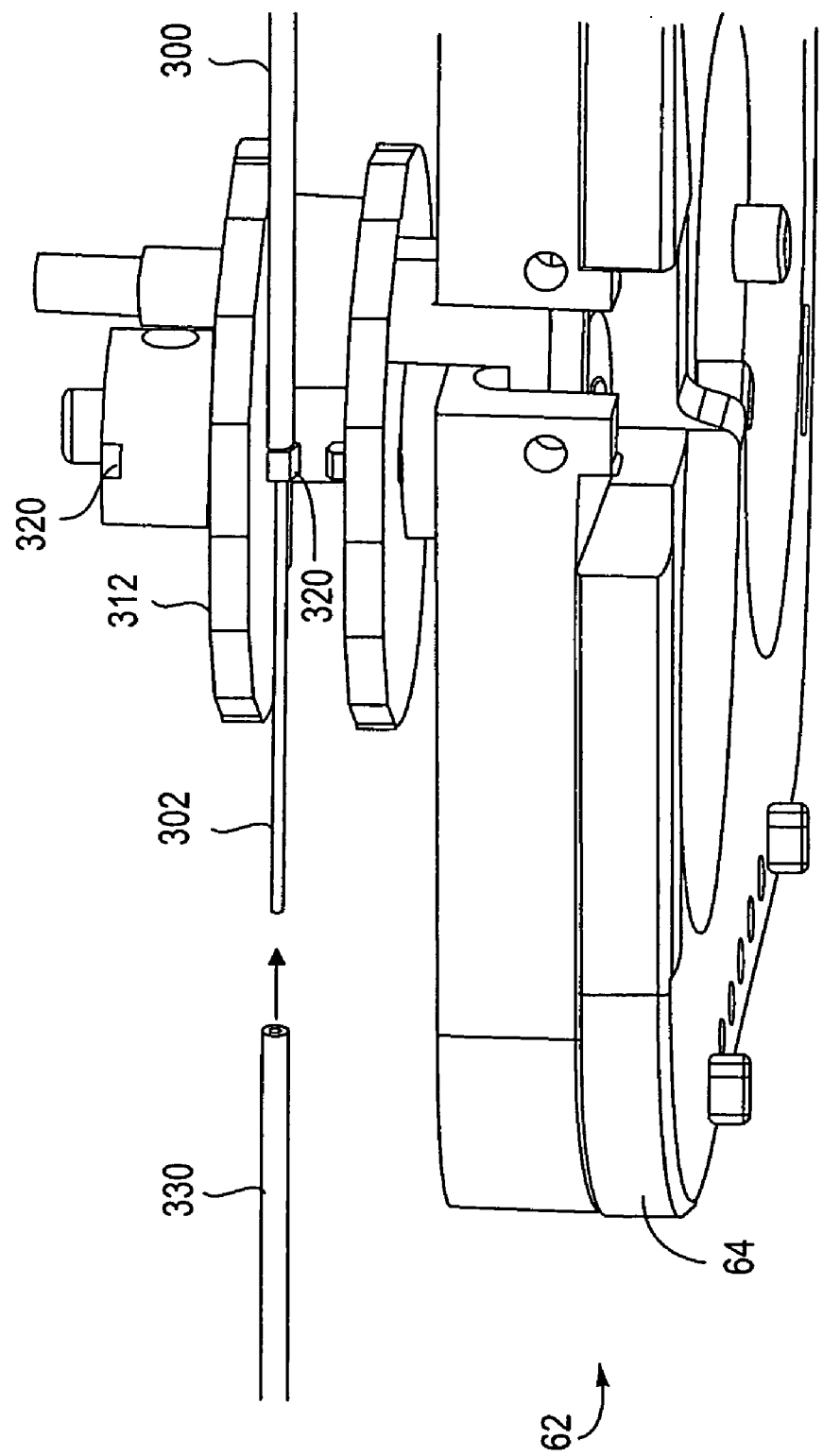
FIG. 29 is a side view illustrating crimping of a crimp onto the wire to maintain positioning of the rod against the pivot pin.

After the wire/rod assembly is advanced through the roll pulley 310, the wire 302 is inserted through the crosshole 324 of a pivot pin 320 as illustrated in FIG. 28. As shown, crossholes 324 of each of the four pivot pins 320 are arranged between the sector gears 312 facing the roll pulley 310. Thus, each of the four rods 300 may be inserted through a separate crosshole 324. It may be appreciated that the number and arrangement of the pivot pins 320 is dependent on the design of the wrist mechanism. Wrist mechanisms having greater or fewer numbers of rods or rods in different arrangements would have corresponding pivot pins 320 to which the rods would be connected. Each crosshole 324 is sized to allow passage of the wire 302 but not the rod 300. Therefore, the rod 300 abuts the flat surface 322 of the pivot pin 320. To maintain position of the wire/rod assembly and abutment of the rod 300 against the flat surface 322, a crimp 330 is slid onto the wire 302, as shown in FIG. 29, and crimped in place.

Figure 30:
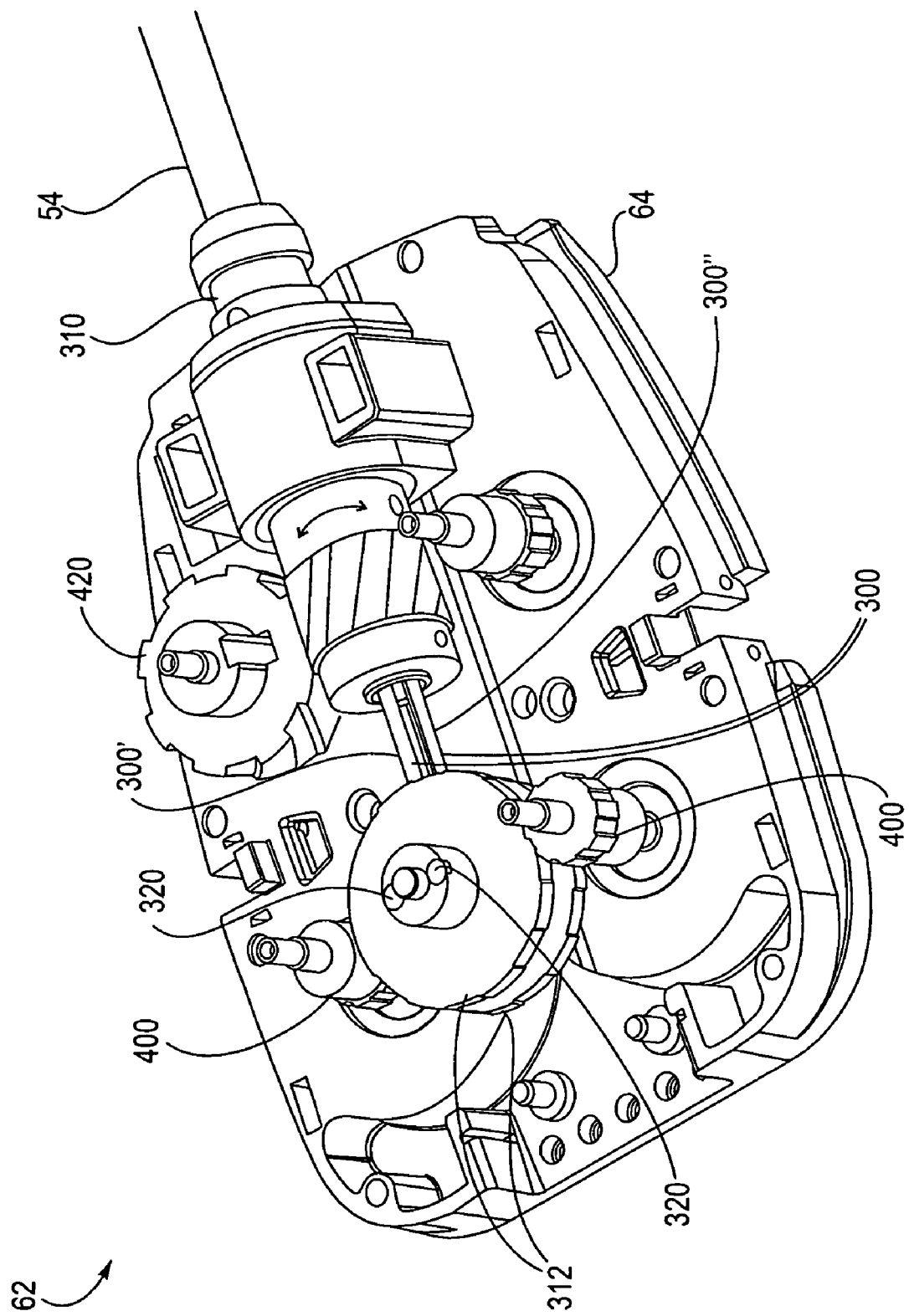
FIG. 30 is a top perspective view of the tool base, including mechanisms to manipulate the rods to actuate the wrist mechanism.

FIG. 30 is a top perspective view of the tool base 62. Rods 300 emerge from the roll pulley 310 and connect with the pins 320 between the sector gears 312 as described above. Manipulation of the rods 300 actuates the wrist mechanism to position the distal clevis in a desired orientation. For example, the sector gears 312 can be individually rotated clockwise or counterclockwise by action of gears 400, as indicated by circular arrows. Such rotation either advances or retracts each rod 300 depending on the position of the rods 300. For example, by rotating the sector gear 312 clockwise, rod 300' is advanced while rod 300" is retracted. As described above, advancement of one rod tips the distal clevis to face away from the advanced rod while, in this embodiment, the rod attached to the distal clevis in the diametrically opposite position is simultaneously retracted. Typically, the one rod is advanced and the diametrically opposite rod is retracted by the same amount. However, it may be appreciated the advancement and retraction of these rods may vary, usually by attaching the rods at different locations on a particular sector gear. In any case, advancement and retraction of the rods provides for the pitch and yaw movements of the distal clevis and attached end effector. The rods 300 can also be rotated by action of gear 420 which rotates the roll pulley 310, as indicated by a curved arrow. The roll pulley 310 rotates the shaft 54 around its central axis 51. This in turn rotates the guide tube 20 to which the shaft 54 is connected. Since the rods 300 pass through guide slots 30 in the guide tube 20 yet are fixed to rotational actuation members at their backends, the guide slots 30 translate the distal ends of the rods 300 in a circular fashion around the central axis 51 while the backends are fixed in place. This is possible by flexing of the rods 300. Due to the length, thickness and flexibility of the rods, 360 degree rotation is possible. This provides for the roll movement of the distal clevis and attached end effector. It may be appreciated that other back end mechanisms may be used to actuate and manipulate the rods 300. For instance, the rods 300 may be independently controlled without the use of rotational actuation members 312.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A robotic surgical tool comprising:
    a distal member configured to support an end effector;
    a plurality of rods mechanically coupled to the distal member and movable generally along an axial direction to adjust an orientation of the distal member with respect to the axial direction; and
    a tool base including a first rotational actuation mechanism mechanically coupled to at least one of the plurality of rods so as to control movement of the at least one rod generally along the axial direction, and a roll actuation mechanism mechanically coupled to the distal member to control rotation of the distal member about the axial direction, wherein first and second rods of the plurality of rods are coupled to the first rotational actuation mechanism so that rotation of the first rotational actuation mechanism in a first direction causes advancement of the first rod and retraction of the second rod, the first rotational actuation mechanism includes a first sector gear and a first pitch/yaw gear, the first sector gear having an axis of rotation and two pivot pins positioned on opposite sides of the axis of rotation, the first and second rods are respectively connected to the two pivot pins so as to advance and retract the first and second rods when the first sector gear is rotated about the axis of rotation, the first pitch/yaw gear engaged with the first sector gear so as to controllably rotate the first sector gear.

2. The robotic surgical tool according to claim 1, wherein rotation of the first rotational actuation mechanism in a second direction causes retraction of the first rod and advancement of the second rod.

3. The robotic surgical tool according to claim 2, further comprising: a second rotational actuation mechanism, wherein third and fourth of the plurality of rods are coupled to the second rotational actuation mechanism so that rotation of the second rotational actuation mechanism in the first direction causes advancement of the third rod and retraction of the fourth rod.

4. The robotic surgical tool according to claim 3, wherein rotation of the second rotational actuation mechanism in the second direction causes retraction of the third rod and advancement of the fourth rod.

5. The robotic surgical tool according to claim 4, wherein the first and second rods are positioned diametrically opposite each other relative to an axis of rotation of the first rotational actuation mechanism, and the third and fourth rods are positioned diametrically opposite to each other relative to an axis of rotation of the second rotational actuation mechanism.

6. The robotic surgical tool according to claim 1, wherein a corresponding pair of the plurality of rods is coupled to the first rotational actuation mechanism in diametrically opposed positions so that rotation of the first rotational actuation mechanism causes the corresponding pair of rods to move in opposite directions.

7. The robotic surgical tool according to claim 6, wherein distal ends of the corresponding pair of the plurality of rods are connected to a base of the distal member so that the distal ends rotate about the axial direction when the distal member is rotated about the axial direction by the roll actuation mechanism.

8. The robotic surgical tool according to claim 7, wherein proximal ends of the corresponding pair of the plurality of rods are substantially held in place so that when the distal member is rotated about the axial direction by the roll actuation mechanism, the proximal ends of the corresponding pair of rods do not substantially rotate about the axial direction and flex to accommodate such rotation.

9. The robotic surgical tool according to claim 1, wherein the roll actuation mechanism comprises:
    a roll pulley mechanically coupled to the distal member so as to rotate the distal member about the axial direction when the roll pulley is rotated; and
    a roll gear engaged with the roll pulley so as to controllably rotate the roll pulley.

10. The robotic surgical tool according to claim 9, wherein the first and second rods pass through an inner passage of the roll pulley in order to mechanically couple to the first rotational actuation mechanism.

11. The robotic surgical tool according to claim 10, further comprising: a second rotational actuation mechanism, wherein third and fourth of the plurality of rods are coupled to the second rotational actuation mechanism so that rotation of the second rotational actuation mechanism in the first direction causes advancement of the third rod and retraction of the fourth rod.

12. The robotic surgical tool according to claim 11, wherein the second rotational actuation mechanism comprises:

a second sector gear having an axis of rotation and two pivot pins positioned on opposite sides of the axis of rotation, wherein the third and fourth rods are respectively connected to the two pivot pins of the second sector gear so as to advance and refract the third and fourth rods when the second sector gear is rotated about the axis of rotation; and a second pitch/yaw gear engaged with the second sector gear so as to controllably rotate the second sector gear.

13. The robotic surgical tool according to claim 12, wherein the plurality of rods are mechanically coupled to corresponding of the pivot pins of the first and second sector gears on facing sides of the first and second sector gears.

14. The robotic surgical tool according to claim 13, wherein the first and second sector gears are mounted on a common sector pivot pin.

* * * * *